United States Patent [19]

Kurashina et al.

[11] Patent Number: 4,877,795
[45] Date of Patent: Oct. 31, 1989

[54] 4H-QUINOLIZIN-4-ONE COMPOUNDS USEFUL FOR THE TREATMENT OF ALLERGIC BRONCHIAL ASTHMA, ALLERGIC RHINITIS ATROPIC DERMATITIS AND THE LIKE

[75] Inventors: Yoshikazu Kurashina; Hiroshi Miyata; Den-ichi Momose, all of Matsumoto, Japan

[73] Assignee: Kissei Pharmaceutical Co., Ltd., Japan

[21] Appl. No.: 147,549

[22] Filed: Jan. 25, 1988

[30] Foreign Application Priority Data

| Jan. 30, 1987 | [JP] | Japan | 62-19734 |
| Jan. 30, 1987 | [JP] | Japan | 62-19735 |
| Jan. 30, 1987 | [JP] | Japan | 62-19736 |
| Jan. 30, 1987 | [JP] | Japan | 62-19737 |
| Feb. 12, 1987 | [JP] | Japan | 62-30603 |
| Feb. 12, 1987 | [JP] | Japan | 62-30604 |
| Feb. 12, 1987 | [JP] | Japan | 62-30605 |

[51] Int. Cl.$^4$ .............. C07D 455/02; A61K 31/435
[52] U.S. Cl. .............................. 514/306; 514/252 546/138; 544/36
[58] Field of Search ............... 546/138; 514/306, 252 544/36

[56] References Cited

U.S. PATENT DOCUMENTS 4,650,804  3/1987  Kitaura et al. ............... 514/306
4,698,349 10/1987  Kitaura et al. ............... 514/306

Primary Examiner—Alan L. Rotman
Attorney, Agent, or Firm—Depaoli & O'Brien

[57] ABSTRACT

This invention provides novel 4H-quinolizin-4-one compounds which exhibit a selective inhibitory activity against IgE-antibody formation, and have utility for treatment of diseases associated with IgE formation in mammals, such as allergic bronchial asthma, allergic rhinitis, atopic dermatitis, hypersensitiveness, and the like.

12 Claims, No Drawings

4H-QUINOLIZIN-4-ONE COMPOUNDS USEFUL FOR THE TREATMENT OF ALLERGIC BRONCHIAL ASTHMA, ALLERGIC RHINITIS ATROPIC DERMATITIS AND THE LIKE

FIELD OF THE INVENTION

This invention relates to novel quinolizinone derivatives having utility as therapeutic agents. More particularly, this invention provides 4H-quinolizin-4-one components which exhibit selective inhibitory activities relative to IgE-antibody formation, and which have properties suitable for application as drugs for diseases associated with IgE such as allergic bronchial asthma, allergic rhinitis, atopic dermatitis, hypersensitiveness, and the like.

BACKGROUND OF THE INVENTION

Several classes of immunoglobulin(s) (hereinafter referred to as Ig(s))' are well known as antibodies concerned with immune response. Most of the Igs, especially immunoglobulin G (hereinafter referred to as IgG) which is one class of Igs, play an important role in self-defense mechanisms in mammals against foreign substances such as viruses, bacteria, tumors, and the like.

However, immunoglobulin E (hereinafter referred to as IgE) which is another class of Igs, has been confirmed to be primarily responsible for diseases such as an allergic bronchial asthma, allergic rhinitis, atopic dermatitis, hypersensitiveness, and the like (Journal of Immunology, Vol. 10, pp 445, 1925, Journal of Immunology, Vol. 97, pp 75, 1966). It also has been confirmed that serum concentrations of IgE in most allergic patients suffering from those diseases in general are higher than those in normal ones.

Therefore, for a causal and useful treatment of such diseases associated with IgE, selective inhibitors of IgE formation are being actively sought. The prospective inhibitors preferably would not inhibit excessively any class of Igs except IgE for reasons mentioned above.

Up to the present time, various compounds have been reported to inhibit IgE formation, in literature such as [Japanese patent application (OPI) Nos. 130516/79 and 76/78 (the term "OPI" used herein refers to an unexamined Japanese patent application); U.S. Pat. No. 4,395,405; European patent application No. 203,435(A2); J. Med. Chem. Vol. 25, No. 12, pages 1495–1499, [1982].

Of particular interest with respect to the present invention are publications which disclose compounds having a substituted 4H-quinolizin-4-one nucleus.

Process embodiments for production of 1-, 2- and 3-substituted 4H-quinolizin-4-one derivatives, specifically methyl 3-cyano-2-methylthio-4H-quinolizin-4-one-1-carboxylate and ethyl 3-cyano-2-methylthio-4H-quinolizin-4-one-1-carboxylate are described in Yakugaku Zasshi, Vol. 89, No. 2, pages 203–208, 1969; ibid. Vol. 90, No. 2, pages 127–131, 1970; ibid. Vol. 91, No. 12, pages 1275–1278, 1971; ibid. Vol. 94, No. 1, pages 44–49, 1974; ibid. Vol. 97, No. 9, pages 1039–1045, 1977; Chem. Pharm. Bull, Vol. 18, No. 1, pages 124–127, 1970; ibid. Vol. 21, No. 5, pages 921–925, 1973; J. Heterocycl. Chem., Vol. 10, No. 2, pages 139–142, 1973; and J. Chem. Soc. (c), pages 1143–1146, 1969.

European patent application No. 157346(A2) and Japanese patent application (OPI) No. 222482/85 which are counterparts of British patent application Nos. 8408292 and 8429710, filed Mar. 30, 1984 and Nov. 23, 1984, respectively, disclose quinolizinone derivatives having an inhibitory activity on allergies and ulcers, which derivatives correspond to the formula:

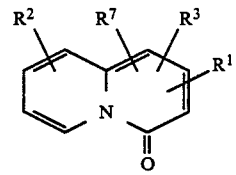

where $R^1$ is carboxy, amidated carboxy, cyano, thiocarbamoyl or tetrazolyl; $R^7$ is hydrogen or aryl; $R^2$ is hydrogen, hydroxy, lower alkyl or lower alkoxy; $R^3$ is hydrogen, hydroxy, lower alkyl, lower alkoxy, lower alkenyloxy, aryl which may have suitable substituents, arylthio, aroyl, ar(lower)alkyl, arenesulfonyl, arylamino which may have a suitable substituent or aryloxy; and $R^2$ and $R^3$ can be located at any place on the quinolizine ring and can be linked together to form $-CH_2CH_2CH_2-$, $-CH=CH-$ or $-CH=CH-CH=CH-$; and pharmaceutically acceptable salts thereof.

Japanese patent application (OPI) No. 77385/87 which is a counterpart of U.S. patent application Ser. No. 770953 filed Aug. 30, 1985, discloses quinolizinone derivatives having inhibitory activity on allergies and ulcers, which correspond to the formula:

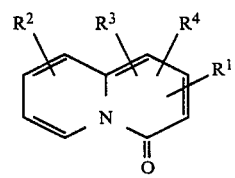

where $R^1$ is carboxy, tetrazolylcarbamoyl or amino-substituted triazolylcarbamoyl; $R^2$ is hydrogen or lower alkoxy; $R^3$ is hydrogen, aroyl, aryl, carboxy or protected carboxy; $R^4$ is hydrogen or hydroxy; with the proviso that (i) when $R^3$ is hydrogen, $R^4$ is hydroxy, (ii) when $R^3$ is aryl, $R^1$ is amino-substituted triazolylcarbamoyl and (iii) when $R^3$ is aroyl, $R^2$ is lower alkoxy; and pharmaceutically acceptable salts thereof.

U.S. Pat. No. 4,650,804 which is a counterpart of British patent application Nos. 8408292 and 8429710, filed Mar. 30, 1984 and Nov. 23, 1984, respectively, disclose quinolizinone derivatives having inhibitory activity on allergies and ulcers, which derivatives correspond to the formula:

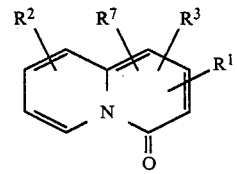

where $R^1$ is tetrazolylcarbamoyl; $R^7$ is hydrogen or aryl selected from phenyl, tolyl, xylyl, cumenyl, naphthyl and biphenylyl; $R^2$ is hydrogen, hydroxy, lower alkyl or lower alkoxy; $R^3$ is hydrogen, hydroxy, lower alkyl, lower alkoxy, lower alkenyloxy, phenyl, naphthyl, biphenylyl, phenyl having one or more substituents selected from halogen lower alkyl and lower alkoxy, arylthio selected from phenylthio, tolylthio, xylylthio, cumenylthio, naphthylthio and biphenylthio, aroyl selected from benzoyl, toluoyl and naphthoyl ar(lower)alkyl selected from phenyl(lower)alkyl, tolyl(lower)alkyl, xylyl(lower)alkyl, cumenyl(lower)alkyl, naphthyl(lower)alkyl and biphenylyl(lower)alkyl, arenesulfonyl selected from benzenesulfonyl and p-toluenesulfonyl, arylamino selected from phenylamino, naphthylamino, biphenylylamino, phenylamino having lower alkyl on the nitrogen atom or aryloxy selected from phenoxy and tolyloxy; or pharmaceutically acceptable salts thereof.

In none of the publications described above is there any disclosure or suggestion that novel substituted 4H-quinolizin-4-one of the type provided by the present invention might exhibit an inhibitory activity against IgE formation in mammals.

SUMMARY OF THE INVENTION

Accordingly, an object of this invention is to provide novel quinolizinone derivatives which exhibit selective inhibitory activities against IgE formation when administered to human or other mammals.

Another object of this invention is to provide pharmaceutical compositions comprising quinolizinone derivatives.

A further object of this invention is to provide methods for treatment of diseases associated with IgE formation, such as allergic bronchial asthma, allergic rhinitis, atopic dermatitis, hypersensitiveness, and the like.

Other objects, features and advantages of this invention will be apparent from the following description of the invention.

The present invention provides novel 4H-quinolizin-4-one derivatives represented by the formula (I):

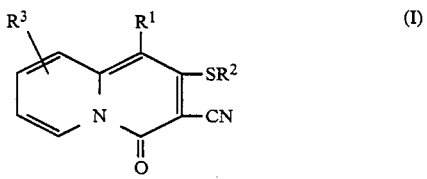

where $R^1$ is an esterified-carboxy, carbamoyl, substituted carbamoyl, cyclic aminocarbonyl or acyl group; $R^2$ is an alkyl, alkenyl or aralkyl group; $R^3$ is hydrogen or an alkyl group; with the proviso that $R^1$ is not methoxycarbonyl or ethoxycarbonyl when $R^2$ is methyl.

In the above and subsequent description of the present specification, the terms used in the definitions of the symbols have the following meanings.

The term "alkyl" and the "alkyl" moiety in "aralkyl" refer to a straight or branched aklyl group having 1 to 6 carbon atoms.

The term "alkenyl" refers to a straight or branched alkenyl group having 2 to 6 carbon atoms, and the term "alkynyl" refers to a straight or branched alkynyl group having 2 to 6 carbon atoms.

The term "cycloalkyl" refers to a saturated cyclic alkyl group having 3 to 12 carbon atoms, such as cyclopropyl, cyclohexyl and cyclooctyl which may have suitable substituents on the ring.

The term "aryl" and the "aryl" moiety in "aryloxy" and "arylthio" refer to a substituted or unsubstituted phenyl or napthyl group having 6 to 18 carbon atoms.

The term "acyl" refers to an aliphatic acyl group such as acetyl, propionyl and cyclohexylacetyl; an aromatic acyl group such as benzoyl which may have suitable substituents on the ring; and an aromatic aliphatic acyl group such as phenylacetyl and phenylpropionyl which may have suitable substituents on the ring and/or chain. An acyl group has a content of 2 to 12 carbon atoms.

The term "cyclic amino" and the "cyclic amino" moiety in "cyclic aminocarbonyl" refer to a 5 or 6 membered cyclic amino group such as 1-pyrrolidinyl, piperidino, morpholino and 1-piperazinyl which may have suitable substituents on the ring. A cyclic amino group has a content of 4 to 12 carbon atoms.

The term "alicyclic alkyl", in addition to "cycloalkyl", refers to a saturated or unsaturated mono-, bi- or tricyclic ring system, with each cyclic ring consisting of 3 to 10 carbon atoms and optionally having suitable substituents on the ring.

The term "esterified-carboxy" refers to a —COOR$^4$ substituent in which $R^4$ is an alkyl, alkenyl, alkynyl, aralkyl, alicyclic alkyl radical, and the like, which can have suitable substituents selected from halogen, hydroxy, lower alkyl, lower alkoxy, cycloalkyl, aryl, aryloxy, arylthio, and the like. An esterified-carboxy(—COOR$^4$) substituent has a content of 2 to 18 carbon atoms.

The term "substituted carbamoyl" refers to a mono- or di-(alkyl, alkenyl, alkynyl, cycloalkyl or aralkyl)-carbamoyl group such as a mono- or di(methyl, ethyl, propyl, butyl, allyl, methallyl, propargyl, cyclohexyl or benzyl)-carbamoyl group. A substituted carbamoyl group has a content of 1 to 18 carbon atoms.

The term "heterocyclyl" refers to an aromatic heterocyclic ring containing one or more hetero atoms such as oxygen, nitrogen or sulfur atoms.

Examples of suitable substituents attached to the groups defined above include hydroxy, alkoxy, halogen, nitro, alkoxycarbonyl, lower alkyl and ar(lower)alkyl substituents.

In general, as appropriate in specific groups, the organic radicals represented by $R^1$, $R^2$ and $R^3$ in the 4H-quinolizin-4-one formula (I) above each have a carbon content of 1–18 carbon atoms.

In another embodiment this invention provides a 4H-quinolizin-4-one compound corresponding to the formula:

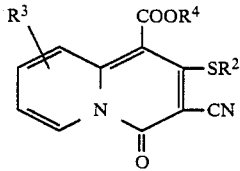

where $R^2$ is an alkyl, alkenyl or aralkyl group having 1 to 18 carbon atoms; $R^3$ is hydrogen or an alkyl group having 1 to 6 carbon atoms; $R^4$ is an aliphatic, alicyclic or aromatic groups having 1 to 16 carbon atoms; with the proviso that $R^4$ is not methyl or ethyl when $R^2$ is methyl.

In another embodiment this invention provides a 4H-quinolizin-4-one compound corresponding to the formula:

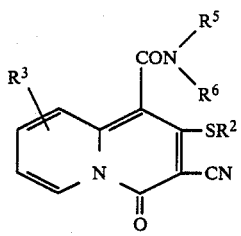

where $R^2$ is an alkyl, alkenyl or aralkyl group having 1 to 18 carbon atoms; $R^3$ is hydrogen or an alkyl group having 1 to 6 carbon atoms; and $R^5$ or $R^6$ individually is hydrogen or an aliphatic, alicyclic or aromatic group having 1 to 8 carbon atoms, or $R^5$ and $R^6$ taken together with the connecting nitrogen atoms form a cycloamino group having 4 to 12 carbon atoms.

In another embodiment this invention provides a 4H-quinolizin-4-one compound corresponding to the formula:

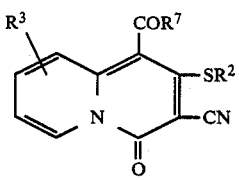

where $R^2$ is an alkyl, alkenyl or aralkyl group having 1 to 18 carbon atoms; $R^3$ is hydrogen or an alkyl group having 1 to 6 carbon atoms; and $R^7$ is an aliphatic, alicyclic or aromatic group having 1 to 12 carbon atoms.

DETAILED DESCRIPTION OF THE INVENTION

The 4H-quinolizin-4-one derivatives of the present invention selectively inhibit the formation of IgE.

Animal test data indicate that the 4H-quinolizin-4-one derivatives of formula (I) of the present invention have potential utility as drugs for diseases associated with IgE, such as allergic bronchial asthma, allergic rhinitis, atopic dermatitis, hypersensitiveness, and the like.

The 4H-quinolizin-4-one derivatives of formula (I) of the present invention can be prepared according to the method described by Kobayashi et al in Yakugaku Zasshi Vol. 89, No. 2, pp 203-208, 1969. In accordance with this method, a 4-one derivative of the present invention corresponding to formula (I):

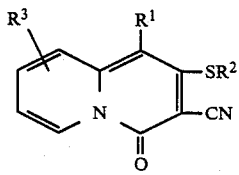

where $R^1$, $R^2$ and $R^3$ are as previously defined, can be prepared by reacting a compound corresponding to the formula:

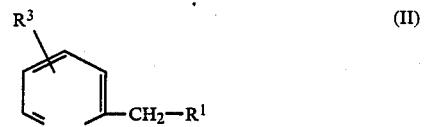

with a compound corresponding to the formula:

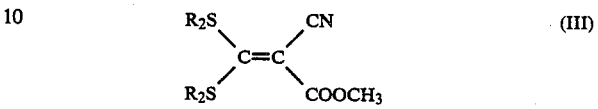

where $R^1$, $R^2$ and $R^3$ in formulae (II) and (III) are as previously defined.

A compound of formula (II) can be prepared according to the manner described in Compendium of Organic Synthetic Methods; Ed. by I. T. Harrison and S. Harison, Wiley-Interscience New York; Vol. 1, pp 272-279, 1971; Peptides; Ed. by E. Scoffone, North Holland Pub. Co. Amsterdam p 17 (1969); Helv. Chim. Acta vol. 45 pp 729-737 (1962).

A compound of formula (III) for use as a starting material can be prepared by a reaction of methyl cyanoacetate, carbon disulfide and a $R^2$—X compound, where S is an acid residual group and $R^2$ has the same meaning as defined above, in accordance with a procedure described in Chemische Berichte, Vol. 95, pp 2861-2870, 1962.

The reaction of a compound of formula (II) with a compound of formula (III) can be conducted in accordance with the following preferred method.

A mixture of a compound of formula (II) and a compound of formula (III) in equal molar quantities is heated at 100°-120° C. for 2-20 hours, with or without the presence of an organic solvent, and then the reaction mixture is subject to conventional product recovery procedures to obtain the 4H-quinolizin-4-one compound produced by the reaction.

The 4H-quinolizin-4-one derivatives represented by formula (I) of the present invention exhibit selective inhibitory activities on IgE formation. The inhibitory activities of the quinolizinone derivatives of formula (I) are confirmed by the determination of Igs produced in cultures of spleen cells from BALB/c mice which exhibit an adoptive secondary immune response against dinitrophenylated proteins of ascaris (DNP-As) according to a procedure described in Cellular Immunology, Vol. 58, pp 188-201, 1981. And the inhibitory activities of the quinolizinone derivatives of formula (I) also are confirmed by the determination of serum concentration of Igs in BALB/c mice which are sensitized by DNP-As according to a procedure described in Immunology, Vol. 21, pp 11-12, 1971.

The results obtained by these tests demonstrate that the compounds of formula (I) of the present invention inhibit IgE formation, and minimally affect the production of Igs other than IgE.

From the results obtained by these animal tests, it can be expected that a compound of formula (I) of the present invention has properties suitable for application as a therapeutic agent for treatment of diseases associated with IgE formation in mammals.

Further, the compounds of formula (I) of the present invention also selectively inhibit IgE production in cultures of peripheral blood lymphocytes from atopic patients.

An acute toxicological test in mice shows that the compounds of formula (I) of the present invention have a very weak toxicity.

The 4H-quinolizin-4-one derivatives of the general formula (I) of the present invention can be administered in various dosage forms depending upon the intended therapy. Typical dosage forms which can be used are tablets, pills, powder, liquid preparations, suspensions, emulsions, granules, capsules, suppositories, and injectable preparations.

In molding the pharmaceutical compositions into a tablet form, a wide variety of conventional carriers known in the art can be used. Examples of suitable carriers are excipients such as glucose, lactose, starch, cacao butter, hardened vegetable oils, kaolin and talc; binders such as gum arabic powder, tragacanth powder, and ethanol; and disintegrants such as laminaria and agar. The tablets, if desired, can be coated and made into sugar-coated tablets, gelatin-coated tablets, film-coated tablets, or tablets coated with two or more layers.

When a pharmaceutical composition is formulated into an injectable preparation, it is preferred that the resulting injectable solution and suspension are sterilized and rendered isotonic with respect to blood. In making the pharmaceutical composition into a solution or suspension, any diluents customarily used in the art can be employed. Examples of suitable diluents include water, ethyl alcohol, propylene glycol, polyoxyethylene sorbitol, and sorbitan esters. Sodium chloride, glucose or glycerol may be incorporated into a therapeutic agent in an amount sufficient to prepare an isotonic solution. The therapeutic agent may further contain ordinary dissolving aids, buffers, pain-alleviating agents, and preservatives, and optionally, coloring agents, fragrances, flavors, sweeteners, and other pharmacologically active agents.

The dosage of the quinolizinone derivatives of the present invention may be in a range of from about 0.1 mg to 10 mg per kg by an oral administration, or from about 0.02 mg to 5 mg per kg by a parenteral administration per day in multiple doses depending upon the type of disease, the severity of condition to be treated, and the like.

In another embodiment this invention provides a method for the treatment of diseases associated with IgE-antibody formation in a mammal which comprises administering an effective dosage of an IgE-formation-inhibiting 4H-quinolizin-4-one compound to the mammal.

In a further embodiment this invention provides a pharmaceutical composition for the treatment of diseases associated with IgE-antibody formation in a mammal, which composition contains an effective dosage of an IgE-formation-inhibiting 4H-quinolizin-4-one compound.

This invention is further illustrated in more detail by way of the following examples and animal test data.

REFERENCE EXAMPLE 1

Cyclohexylmethyl 2-pyridylacetate (R-1)

To a mixture of 422 mg of 2-pyridylacetic acid hydrochloride and 596 μl of cyclohexylmethanol in 5 ml of dry pyridine was added 651 mg of 1,3-dicyclohexylcarbodiimide, and the mixture was stirred for 10 hours at room temperature. The precipitates were filtered off and the filtrate was evaporated under reduced pressure. The residue was dissolved in 20 ml of a 1N-hydrochloric acid, acidic solution was washed twice with 25 ml of diethyl ether. A 2N-aqueous sodium hydroxide was added to the solution to a pH of 11. A separated oil was extracted with 50 ml of dichloromethane, and the organic layer was dried over anhydrous sodium sulfate, the solvent was evaporated under reduced pressure to obtain 525 mg of cyclohexylmethyl 2-pyridylacetate as an oil.

NMR (CDCl$_3$): δ 0.85–1.80(m, 11H), 3.85(s, 2H), 3.93(d, 2H), 7.19(dd, 1H), 7.29(d, 1H), 7.66(dt, 1H). 8.56(d, 1H)

REFERENCE EXAMPLE 2

The following compounds were obtained according to the same procedure as that described in Reference Example 1.

(1) Cyclopropylmethyl 2-pyridylacetate, (R-2),

NMR (CDCl$_3$): δ 0.29(m, 2H), 0.55(m, 2H), 1.13(m, 1H), 3.88(s, 2H), 3.96(d, 2H), 7.21(dd, 1H), 7.32(d, 1H), 7.67(dt, 1H), 8.56(d, 1H)

(2) 2',2',2'-Trichloroethyl 2-pyridylacetate, (R-3),

NMR (CDCl$_3$): δ 4.00(s, 2H), 4.79(s, 2H), 7.22(dd, 1H), 7.34(d, 1H), 7.68(dt, 1H), 8.58(d, 1H)

(3) Isopentyl 2-pyridylacetate, (R-4),

NMR (CDCl$_3$): δ 0.89(d, 6H), 1.51(q, 2H), 1.63(m, 1H), 3.84(s, 2H), 4.16(t, 2H), 7.18(dd, 1H), 7.29(d, 1H), 7.65(dt, 1H), 8.56(d, 1H)

(4) 2'-Propynyl 2-pyridylacetate, (R-5),

NMR (CDCl$_3$): δ 2.47(t, 1H), 3.91(s, 2H), 4.74(d, 2H), 7.20(dd, 1H), 7.31(d, 1H), 7.68(dt, 1H), 8.57(d, 1H)

(5) 2'-Propenyl 2-pyridylacetate, (R-6),

NMR (CDCl$_3$): δ 3.88(s, 2H), 4.63(m, 2H), 5.20–5.34(m, 2H), 5.85–6.00(m, 1H), 7.21(dd, 1H), 7.30(d, 1H), 7.66(dt, 1H), 8.57(d, 1H)

(6) 3'-Cyclohexylpropyl 2-pyridylacetate, (R-7),

NMR (CDCl$_3$): δ 0.75–2.75(m, 15H), 3.84(s, 2H), 4.11(t, 2H), 7.19(dd, 1H), 7.30(d, 1H), 7.64(dt, 1H), 8.56(d, 1H)

(7) Cyclopentyl 2-pyridylacetate, (R-8),

NMR (CDCl$_3$): δ 1.20–1.95(m, 8H), 3.81(s, 2H), 5.21(m, 1H), 7.18(dd, 1H), 7.28(d, 2H), 8.56(d, 1H)

(8) Cyclobutyl 2-pyridylacetate, (R-9),

NMR (CDCl$_3$): δ 1.10–2.41(m, 6H), 3.85(s, 2H), 5.03(m, 1H), 7.18(dd, 1H), 7.29(d, 1H), 7.65(dt, 1H), 8.56(d, 1H)

(9) Cyclohexyl 2-pyridylacetate, (R-10),

NMR (CDCl$_3$): δ 1.19–1.90(m, 10H), 3.84(s, 2H), 4.81(m, 1H), 7.18(dd, 1H), 7.30(d, 1H), 7.66(dt, 1H), 8.56(d,

(10) 2'-Cyclohexenyl 2-pyridylacetate, (R-11),

NMR (CDCl$_3$): δ 1.60–2.18(m, 6H), 3.85(s, 2H), 5.33(m, 1H), 5.72(m, 1H), 5.94(m, 1H), 7.18(dd, 1H), 7.30(d, 1H), 7.65(dt, 1H), 8.56(d, 1H)

(11) trans-4'-Hydroxycyclohexyl 2-pyridylacetate, (R-12),

NMR (CDCl$_3$): δ 1.23–1.58(m, 5H), 1.80–2.06(m, 4H), 3.71(m, 1H), 3.83(s, 2H), 4.81(m, 1H), 7.19(dd, 1H), 7.29(d, 1H), 7.66(dt, 1H), 8.55(d, 1H)

(12) 2'-Methylcyclohexyl 2-pyridylacetate, (R-13),

NMR (CDCl$_3$): δ 0.79 and 0.83(d, 3H), 0.95–2.05(m, 9H), 3.84 and 3.86(s, 2H), 4.45 and 4.96(m, 1H), 7.18(dd, 1H), 7.31(d, 1H), 7.65(m, 1H), 8.56(d, 1H)

(13) Cyclohexyl 4-methyl-2-pyridylacetate, (R-14),

NMR (CDCl$_3$): δ 1.17–1.90(m, 10H), 2.34(s, 3H), 3.78(s, 2H), 4.81(m, 1H), 7.00(d, 1H), 7.11(s, 1H), 8.40(d, 1H)

(14) Cycloheptyl 2-pyridylacetate, (R-15),

NMR (CDCl₃): δ 1.20–1.95(m, 12H), 3.80(s, 2H), 4.98(m, 1H), 7.18(dd, 1H), 7.30(d, 1H), 7.65(dt, 1H), 8.55(d, 1H)

(15) Cyclooctyl 2-pyridylacetate, (R-16),

NMR (CDCl₃): δ 1.25–1.88(m, 14H), 3.81(s, 2H), 4.99(m, 1H), 7.18(dd, 1H), 7.29(d, 1H), 7.65(dt, 1H), 8.56(d, 1H)

(16) 2′-Adamantyl 2-pyridylacetate, (R-17),

NMR (CDCl₃): δ 1.45–2.03(m, 14H), 3.89(s, 2H), 4.97(m, 1H), 7.19(dt, 1H), 7.32(d, 1H), 7.66(dt, 1H), 8.56(d, 1H)

(17) 1′,2′,3′,4′-Tetrahydro-1′-naphthyl 2-pyridylacetate, (R-18),

NMR (CDCl₃): δ 1.67–2.06(m, 4H), 2.66–2.91(m, 2H), 3.87(s, 2H), 6.05(t, 1H), 7.09–7.31(m, 6H), 7.64(dt, 1H), 8.56(d, 1H)

(18) 4′-Bromobenzyl 2-pyridylacetate, (R-19),

NMR (CDCl₃): δ 3.89(s, 2H), 5.11(s, 2H), 7.15–7.53(m, 6H), 7.66(dt, 1H), 8.57(d, 1H)

(19) 1′-Phenylethyl 2-pyridylacetate, (R-20),

NMR (CDCl₃): δ 1.54(d, 3H), 3.87(brs, 2H), 5.93(q, 1H), 7.15–7.42(m, 7H), 7.64(dt, 1H), 8.56(d, 1H)

(20) 3′,4′-Dimethylbenzyl 2-pyridylacetate, (R-21),

NMR (CDCl₃): δ 2.25(s, 6H), 3.89(s, 2H), 5.11(s, 2H), 7.05–7.31(m, 5H), 7.65(dt, 1H), 8.57(d, 1H)

(21) Piperonyl 2-pyridylacetate, (R-22),

NMR (CDCl₃): δ 3.88(s, 2H), 5.07(s, 2H), 5.95(s, 2H), 6.75–6.90(m, 3H), 7.19(dd, 1H), 7.28(d, 1H), 7.65(dt, 1H), 8.57(d, 1H)

(22) 3′,4′,5′-Trimethoxybenzyl 2-pyridylacetate, (R-23),

NMR (CDCl₃): δ 3.83(s, 6H), 3.87(s, 3H), 3.91(s, 2H), 5.11(s, 2H), 6.54(s, 2H), 7.20(dd, 1H), 7.30(d, 1H), 7.66(dt, 1H), 8.56(d, 1H)

(23) Benzyl 4-methyl-2-pyridylacetate, (R-24),

NMR (CDCl₃): δ 2.32(brs, 3H), 3.85(s, 2H), 5.17(s, 2H), 7.00(d, 1H), 7.09(s, 1H), 7.26–7.35(m, 5H), 8.41(d, 1H)

(24) Benzyl 2-pyridylacetate, (R-25),

NMR (CDCl₃): δ 3.91(s, 2H), 5.18(s, 2H), 7.19(dd, 1H), 7.26–7.40(m, 6H), 7.65(dt, 1H), 8.57(d, 1H)

(25) 1′-Bromophenyl)ethyl 2-pyridylacetate, (R-26),

NMR (CDCl₃): δ 1.51(d, 3H), 3.86(s, 2H), 5.87(q, 1H), 7.10–7.48(m, 6H), 7.64(dt, 1H), 8.55(d, 1H)

(26) 4′-Methoxybenzyl 2-pyridylacetate, (R-27),

NMR (CDCl₃): δ 3.80(s, 3H), 3.87(s, 2H), 5.11(s, 1H), 6.87(d, 2H), 7.18(dd, 1H), 7.21–7.31(m, 3H), 7.64(dt, 1H), 8.56(d, 1H)

(27) 1′-(4-Cyanophenyl)ethyl 2-pyridylacetate, (R-28),

NMR (CDCl₃): δ 1.53(d, 3H), 3.89(s, 2H), 5.92(q, 1H), 7.22(dd, 1H), 7.27(d, 1H), 7.39(d, 2H), 7.61(d, 2H), 7.66(dt, 1H), 8.56(d, 1H)

(28) 4′-Ethoxybenzyl 2-pyridylacetate, (R-29),

NMR (CDCl₃): δ 1.41(t, 3H), 4.01(s, 2H), 4.02(q, 2H), 5.11(s, 2H), 6.86(d, 2H), 7.26(d, 2H), 7.31(dd, 1H), 7.41(d, 1H), 7.80(dt, 1H), 8.58(d, 1H)

(29) 4′-Fluorobenzyl 2-pyridylacetate, (R-30), NMR (CDCl₃): δ 3.87(s, 2H), 5.11(s, 2H), 6.99(m, 2H), 7.17(dd, 1H), 7.29(m, 3H), 7.61(dt, 1H), 8.53(d, 1H)

(30) 3′-Methoxybenzyl 2-pyridylacetate, (R-31),

NMR (CDCl₃): δ 3.77(s, 3H), 3.89(s, 2H), 5.14(s, 2H), 6.77–7.33(m, 6H), 7.63(dt, 1H), 8.54(d, 1H)

(31) 4′-Isopropylbenzyl 2-pyridylacetate, (R-32),

NMR (CDCl₃): δ 1.24(d, 6H), 2.89(m, 1H), 3.88(s, 2H), 5.14(s, 2H), 7.13–7.33(m, 6H), 7.62(dt, 1H), 8.55(d, 1H)

(32) 2′-Methoxybenzyl 2-pyridylacetate, (R-33),

NMR (CDCl₃): δ 3.80(s, 3H), 3.90(s, 2H), 5.23(s, 2H), 6.85–6.98(m, 2H), 7.19(dd, 1H), 7.23–7.33(m, 3H), 7.63(dt, 1H), 8.55(d, 1H)

(33) 3′-Chlorobenzyl 2-pyridylacetate, (R-34),

NMR (CDCl₃): δ 3.90(s, 2H), 5.13(s, 2H), 7.15–7.38(m, 6H), 7.65(dt, 1H), 8.56(d, 1H)

(34) 1′-Chlorobenzyl 2-pyridylacetate, (R-35),

NMR (CDCl₃): δ 3.93(s, 2H), 5.28(s, 2H), 7.16–7.38(m, 6H), 7.65(dt, 1H), 8.56(d, 1H)

(35) 4′-Phenylbenzyl 2-pyridylacetate, (R-36),

NMR (CDCl₃): δ 3.92(s, 2H), 5.22(s, 2H), 7.20(dd, 1H), 7.30(d, 1H), 7.35–7.63(m, 9H), 7.66(dt, 1H), 8.58(d, 1H)

(36) 2′-Naphthylmethyl 2-pyridylacetate, (R-37),

NMR (CDCl₃): δ 3.93(s, 2H), 5.34(s, 2H), 7.20(dd, 1H), 7.30(d, 1H), 7.39–7.53(m, 3H), 7.65(dt, 1H), 7.78–7.88(m, 4H), 8.58(d, 1H)

(37) 1′-Naphthylmethyl 2-pyridylacetate, (R-38),

NMR (CDCl₃): δ 3.90(s, 2H), 5.63(s, 2H), 7.13–8.00(m, 10H), 8.56(d, 1H)

(38) 1′-Methyl-2′-phenylethyl 2-pyridylacetate, (R-39),

NMR (CDCl₃): δ 1.23(d, 3H), 2.75(dd, 1H), 2.92(dd, 1H), 3.79(s, 2H), 5.17(m, 1H), 7.10–7.30(m, 7H), 7.62(dt, 1H), 8.55(d, 1H)

(39) 2′,2′-Diphenylethyl 2-pyridylacetate, (R-40),

NMR (CDCl₃): δ 3.76(s, 2H), 4.53(t, 1H), 4.67(d, 2H), 7.03–7.33(m, 12H), 7.54(dt, 1H), 8.50(d, 1H)

(40) 3′-Phenylpropyl 2-pyridylacetate, (R-41),

NMR (CDCl₃): δ 1.95(m, 2H), 2.64(t, 2H), 3.86(s, 2H), 4.15(t, 2H), 7.11–7.31(m, 7H), 7.67(dt, 1H), 8.57(d, 1H)

(41) 1′-Methyl-3′-phenylpropyl 2-pyridylacetate, (R-42),

NMR (CDCl₃): δ 1.26(d, 3H), 1.85(m, 2H), 2.58(m, 2H), 3.83(s, 2H), 4.98(m, 1H), 7.10–7.32(m, 7H), 7.66(dt, 1H), 8.57(d, 1H)

(42) trans-Cinnamyl 2-pyridylacetate, (R-43),

NMR (CDCl₃): δ 3.90(s, 2H), 4.79(m, 2H), 6.29(dt, 1H), 6.64(d, 1H), 7.18–7.41(m, 7H), 7.67(dt, 1H), 8.58(d, 1H)

(43) 2′-Phenylethyl 2-pyridylacetate, (R-44),

NMR (CDCl₃): δ 2.93(t, 2H), 3.83(s, 2H), 4.34(t, 2H), 7.14–7.30(m, 7H), 7.63(dt, 1H), 8.56(d, 1H)

(44) 4′-Phenylbutyl 2-pyridylacetate, (R-45),

NMR (CDCl₃): δ 1.65(m, 4H), 2.61(t, 2H) 3.84(s, 2H), 4.15(t, 2H), 7.13–7.30(m, 7H), 7.64(dt, 1H), 8.55(d, 1H)

(45) 2′-Phenylethyl 4-methyl-2-pyridylacetate, (R-46),

NMR (CDCl₃): δ 2.33(brs, 3H), 2.93(t, 2H), 3.86(s, 2H), 4.34(t, 2H), 7.00–7.35(m, 7H), 8.41(d, 1H)

(46) 3′-Phenylpropyl 4-methyl-2-pyridylacetate, (R-47),

NMR (CDCl₃): δ 1.95(m, 2H), 2.34(s, 3H), 2.64(t, 2H), 3.81(s, 2H), 4.14(s, 2H), 7.00–7.30(m, 7H), 8.42(d, 1H)

(47) 2′-(4-Chlorophenoxy)ethyl 2-pyridylacetate, (R-48),

NMR (CDCl₃): δ 3.90(s, 2H), 4.14(t, 2H), 4.48(t, 2H), 6.81(d, 2H), 7.15–7.30(m, 4H), 7.64(dt, 1H), 8.54(d, 1H)

(48) 3′-Phenoxypropyl 2-pyridylacetate, (R-49),

NMR (CDCl₃): δ 2.11(m, 2H), 3.86(s, 2H), 3.99(t, 2H), 4.33(t, 2H), 6.86(d, 2H), 6.94(t, 1H), 7.17(dt, 1H), 7.24–7.30(m, 3H), 7.62(dt, 1H), 8.54(d, 1H)

(49) 2′-Phenylthioethyl 2-pyridylacetate, (R-50),

NMR (CDCl₃): δ 3.14(t, 2H), 3.82(s, 2H), 4.29(t, 2H), 7.17–7.43(m, 7H), 7.65(dt, 1H), 8.56(d, 1H)

REFERENCE EXAMPLE 3

Isopropyl 2-pyridylacetate, (R-51),

In a solution of 355 mg of 2-pyridylacetic acid hydrochloride in 5 ml of 2-propanol, hydrogen chloride was saturated at 0° C., and the solution was stirred for 10 hours at room temperature. Sodium bicarbonate was added to the reaction mixture to make alkaline, and the solution was extracted with 50 ml of diethyl ether. The ethereal layer was washed successively with water and a suturated aqueous sodium chloride solution, and dried over anhydrous sodium sulfate, and the solvent was evaporated under reduced pressure to give 305 mg of isopropyl 2-pyridylacetate as an oil.

NMR (CDCl$_3$): δ 1.24(d, 6H), 3.82(s, 2H), 5.06(m, 1H), 7.19(dt, 1H), 7.30(d, 1H), 7.66(dt, 1H), 8.56(d, 1H)

REFERENCE EXAMPLE 4

The following compounds were obtained according to the same procedure as that described in Reference Example 3.

(1) Propyl 2-pyridylacetate, (R-52),

NMR (CDCl$_3$): δ 0.90(t, 3H), 1.65(m, 2H), 3.86(s, 2H), 4.09(t, 2H), 7.19(dt, 1H), 7.30(d, 1H), 7.66(dt, 1H), 8.56(d, 1H)

(2) Butyl 2-pyridylacetate, (R-53),

NMR (CDCl$_3$): δ 0.90(t, 3H), 1.34(m, 2H), 1.63(m, 2H), 3.85(s, 2H), 4.13(t, 2H), 7.19(dd, 1H), 7.30(d, 1H), 7.66(dt, 1H), 8.56(d, 1H)

(3) 1'-Methylpropyl 2-pyridylacetate, (R-54),

NMR (CDCl$_3$): δ 0.85(t, 3H), 1.21(d, 3H), 1.43-1.70(m, 2H), 3.84(s, 2H), 4.90(m, 1H), 7.20(dd, 1H), 7.31(d, 1H), 7.67(dt, 1H), 8.55(d, 1H)

REFERENCE EXAMPLE 5

N,N-Dibenzyl-2-pyridylacetamide, (R-55),

To a solution of 413 mg of 2-pyridylacetic acid hydrochloride, 470 mg of dibenzylamine and 321 mg of 1-hydroxybenzotriazole in 5 ml of dry pyridine was added 637 mg of 1,3-dicyclohexylcarbodiimide, and the mixture was stirred for 15 hours at room temperature. Precipitates were filtered off, the filtrate was concentrated under reduced pressure. The residue was dissolved in a 1N-hydrochloric acid and washed twice with 25 ml of diethyl ether, and then a 2N-aqueous hydroxide was added to the solution to a pH of 11. A separated oil was extracted with 50 ml of dichloromethane, and the organic layer was dried over anhydrous sodium sulfate, and the solvent was evaporated under reduced pressure to give 486 mg of N,N-dibenzyl-2-pyridylacetamide as an oil.

NMR (CDCl$_3$): δ 4.02(s, 2H), 4.61(d, 4H), 7.10-7.41(m, 12H), 7.65(dt, 1H), 8.51(d, 1H)

REFERENCE EXAMPLE 6

The following compounds were obtained according to the same procedure as that described in Reference Example 5.

(1) N,N-Dicyclohexyl-2-pyridylacetamide, (R-56),

NMR (CDCl$_3$): δ 1.00-1.80(m, 18H), 2.48(m, 2H), 2.87(m, 1H), 3.70(m, 1H), 3.90(s, 2H), 7.14(dd, 1H), 7.34(d, 1H), 7.62(dt, 1H), 8.52(d, 1H)

(2) N,N-Diethyl-2-pyridylacetamide, (R-57),

NMR (CDCl$_3$): δ 1.12(m, 6H), 3.40(m, 4H), 3.90(s, 2H), 7.16(dd, 1H), 7.38(d, 1H), 7.64(dt, 1H), 8.52(d, 1H)

(3) N,N-Diisopropyl-2-pyridylacetamide, (R-58),

NMR (CDCl$_3$): δ 1.04(d, 6H), 1.40(d, 6H), 3.90(s, 2H), 7.15(dd, 1H), 7.36(d, 1H), 7.64(dt, 1H), 8.52(d, 1H) 048777957

(4) N,N-Diisobutyl-2-pyridylacetamide, (R-59),

NMR (CDCl$_3$): δ 0.83(d, 6H), 0.91(d, 6H), 1.99(m, 2H), 3.21(d, 4H), 3.93(s, 2H), 7.14(dd, 1H), 7.37(d, 1H), 7.62(dt, 1H), 8.51(d, 1H)

(5) N,N-Dihexyl-2-pyridylacetamide, (R-60),

NMR (CDCl$_3$): δ 0.88(m, 6H), 1.27(br, 12H), 1.49(m, 4H), 3.31(m, 4H), 3.89(s, 2H), 7.16(dd, 1H), 7.37(d, 1H), 7.63(dt, 1H), 8.52(d, 1H)

(6) N-Benzyl-N-methyl-2-pyridylacetamide, (R-61),

NMR (CDCl$_3$): δ 2.95 and 3.00(s, 3H), 3.97 and 4.00(s, 2H), 4.62 and 4.69(s 2H), 7.08-7.41(m, 7H), 7.64(m, 1H), 8.49 and 8.54(d. 1H)

(7) N-Phenyl-N-(2-phenylaminoethyl)-2-pyridylacetamide,(R-62),

NMR (CDCl$_3$): δ 3.29(t, 2H), 3.66(s, 2H), 4.04(t, 2H), 6.57(d, 2H), 6.68(t, 1H), 7.10-7.40(m, 9H), 7.57(dt, 1H), 8.49(d, 1H)

(8) N-Benzyl-N-isopropyl-2-pyridylacetamide, (R-63),

NMR (CDCl$_3$): δ 1.04 and 1.11(d, 6H), 3.79 and 4.06(s, 2H), 4.54 and 4.62(s, 2H), 4.44 and 4.84(m, 1H), 7.10-7.70(m, 8H), 8.49 and 8.55(d, 1H)

(9) N-Cyclohexyl-N-isopropyl-2-pyridylacetamide, (R-64),

NMR (CDCl$_3$): δ 1.05 and 1.38(d, 6H), 0.90-1.82(m, 9H), 2.47(br, 1H), 2.91 and 3.37(br, 1H), 3.69 and 4,18(m, 1H), 7.15(dd, 1H), 7.35(d, 1H), 7.63(dt, 1H), 8.52(d, 1H)

(10) N-Allyl-N-cyclohexyl-2-pyridylacetamide, (R-65),

NMR (CDCl$_3$): δ 0.95-1.85(m, 10H), 3.85(s, 2H), 3.88 and 4,42(m, 1H), 3.97(s, 2H), 5.00-5.30(m, 2H), 5.82(m, 1H), 7.15(m, 1H), 7.35(t, 1H), 7.63(m, 1H), 8.52(m, 1H)

(11) N-(3-Phenylpropyl)-2-pyridylacetamide, (R-66),

NMR (CDCl$_3$): δ 1.82(m, 2H), 2.59(t, 2H), 3.28(q, 2H), 7.10-7.40(m, 8H), 7.66(dt, 1H), 8.56(d, 1H)

(12) N-Cyclohexyl-2-pyridylacetamide, (R-67),

NMR (CDCl$_3$): δ 1.10-1.90(m, 10H), 3.71(s, 2H), 3.75(m, 1H), 7.15(br, 1H), 7.23(dd, 1H), 7.32(d, 1H), 7.69(dt, 1H), 8.55(d, 1H)

(13) N-Benzyl-2-pyridylacetamide, (R-68),

NMR (CDCl$_3$): δ 3.79(s, 2H), 4.47(s, 2H), 7.17-7.37(m, 8H), 7.67(dt, 1H), 8.51(d, 1H)

(14) N-(4-Anilinophenyl)-2-pyridylacetamide, (R-69),

NMR (CDCl$_3$): δ 3.86(s, 2H), 5.66(br, 1H), 6.87(t, 1H), 6.97-7.06(m, 4H), 7.20-7.26(m, 3H), 7.31(d, 1H), 7.44(d, 2H), 7.70(dt, 1H), 8.01(br, 1H), 8.61(d, 1H)

(15) N-(4-Phenyl-2-thiazolyl)-2-pyridylacetamide (R-70),

NMR (CDCl$_3$): δ 3.99(s, 2H), 7.12(s, 1H), 7.27-7.43(m, 5H), 7.72(dt, 1H), 7.86(d, 2H), 8,72(dd, 1H)

(16) N-(1,2,3,4-Tetrahydro-2-naphthyl)-2-pyridylacetamide, (R-71),

NMR (CDCl$_3$): δ 1.67-2.10(m, 4H), 2.77(m, 2H), 3.78(s, 2H), 5.17(m, 1H), 7.15-7.33)m, 6H), 7.43(br, 1H), 7.67(dt, 1H), 8.46(d, 1H)

(17) N-(4-Methoxycarbonylbenzyl)-2-pyridylacetamide, (R-72),

NMR (CDCl$_3$): δ 3.83(s, 2H), 3.90(s, 3H), 4.52(d, 2H), 7.20-7.47(m, 5H), 7.71(m, 1H), 7.82-8.00(m, 2H), 8.51 and 8.60(d, 1H)

(18) 4-Phenyl-1-(2-pyridylacetyl)piperidine, (R-73),

NMR (CDCl$_3$): δ 1.50–1.95(m, 4H), 2.58–2.80(m, 2H), 3.11(m, 1H), 3.98(s, 2H), 4.23(m, 1H), 4.79(m, 1H), 7.10–7.37(m, 6H), 7.39(d, 1H), 7.66(dt, 1H), 8.53(d, 1H)

(19) 1-(2-pyridylacetyl)piperidine, (R-74),

NMR (CDCl$_3$): δ 1.35–1.65(m, 6H), 3.48–3.60(m, 4H), 3.93(s, 2H), 7.16(dd, 1H), 7.36(d, 1H), 7.64(dt, 1H), 8.52(d, 1H)

(20) 4-Acetoxy-4-phenyl-1-(2-pyridylacetyl)piperidine, (R-75),

NMR (CDCl$_3$):

δ 1.86(m, 1H), 1.90(s, 3H), 2.06(m, 1H), 2.72–2.32(m, 2H), 3.16(m, 1H), 3.33(m, 1H), 3.82(dt, 1H), 3.92(s, 2H), 4.20(dt, 1H), 7.17(dd, 1H), 7.23–7.40(m, 6H), 7.64(dt, 1H), 8.51(d, 1H)

(21) 4-Benzyl-1-(2-pyridylacetyl)piperidine, (R-76),

NMR (CDCl$_3$): δ 0.88–1.26(m, 2H), 1.57–1.80(m, 3H), 2.50(d, 2H), 2.51(m, 1H), 2.92(dt, 1H), 3.93(s, 2H), 4.06(m, 1H), 4.61(m, 1H), 7.08–7.36(m, 7H), 7.64(dt, 1H), 8.53(d, 1H)

(22) 1-(3-Methyl-2-pyridylacetyl)-4-phenylpiperidine, (R-77),

NMR (CDCl$_3$): δ 1.47–1.95(m, 4H), 2.37(s, 3H), 2.71(m, 2H), 3.14(dt, 1H), 3.98(s, 2H), 4.23(m, 1H), 4.81(m, 1H), 7.09(dd, 1H), 7.16–7.35(m, 6H), 7.47(d, 1H), 8.38(d, 1H)

(23) 1-(2-Pyridylacetyl)perhydroindole, (R-78),

NMR (CDCl$_3$): δ 1.05–2.40(m, 11H), 3.45–4.12(m, 3H), 3.82 and 3.90(s, 2H), 7.17(dd, 1H), 7.37 and 7.42(d, 1H), 7,64(t, 1H), 8.51(d, 1H)

(24) 1-(2-Pyridylacetyl)perhydroquinoline, (R-79),

NMR (CDCl$_3$): δ 1.05–1.85(m, 13H), 2.61 and 2.98(dt, 1H), 3.84 and 4.02(m, 1H), 3.92 and 3.96(s and d, 2H), 4.50 and 4.66(m, 1H), 7.16(dt, 1H), 7.36(t, 1H), 7.64(dt, 1H), 8.52(m, 1H)

(25) 2-(2-Pyridylacetyl)-1,2,3,4-tetrahydroisoquinoline, (R-80),

NMR (CDCl$_3$): δ 2.75 and 2.86(t, 2H), 3.84(m, 2H), 4.01(s, 2H), 4.87(m, 2H), 7.03–7.22(m, 5H), 7.36(t, 1H), 7.62(q, 1H), 8.53(t, 1H)

(26) 1-(2-Pyridylacetyl)-1,2,3,4-tetrahydroquinoline, (R-81),

NMR (CDCl$_3$): δ 1.94(m, 2H), 2.70(m, 2H), 3.87(m, 2H), 4.08(s, 2H), 7.05–7.35(m, 6H), 7.62(t, 1H), 8.53(d, 1H)

(27) 1-Piperonyl-4-(2-pyridylacetyl)piperazine, (R-82),

NMR (CDCl$_3$): δ 2.28(t, 2H), 2.37(t, 2H), 3.38(s, 2H), 3.57(t, 2H), 3.65(t, 2H), 3.93(s, 2H), 5.95(s, 2H), 6.73(m, 2H), 6.83(s, 1H), 7.18(dd, 1H), 7.34(d, 1H), 7.65(dt, 1H), 8.51(d, 1H)

(28) 1-Benzyl-4-(2-pyridylacetyl)piperazine, (R-83),

NMR (CDCl$_3$): δ 2.31(t, 2H), 2.40(t, 2H), 3.48(s, 2H), 3.59(t, 2H), 3.66(t, 2H), 3.93(s, 2H), 7.17(dt, 1H), 7.22–7.37(m, 6H), 7.64(dt, 1H), 8.52(d, 1H)

(29) 1-Phenyl-4-(2-pyridylacetyl)piperazine, (R-84),

NMR (CDCl$_3$): δ 3.04(t, 2H), 3.12(t, 2H), 3.79(m, 4H), 3.98(s, 2H), 6.85–6.95(m, 3H), 7.16–7.40(m, 4H), 7.66(dt, 1H), 8.53(d, 1H)

REFERENCE EXAMPLE 7

Methyl 2-pyridylmethyl ketone, (R-85),

To a solution of 960 mg of n-butyllithium in diethyl ether was added dropwise 1480 μl of α-picoline at 0° C. under an argon and the reaction mixture was stirred for 10 minutes at 0° C. To the reaction mixture was added 782 l of acetonitrile and the mixture was stirred for 3 hours at room temperature, followed by extraction with 30 ml of 1.5N-sulfuric acid. The acidic solution was washed with 25 ml of diethyl ether, and made alkaline with a 2N-aqueous sodium hydroxide solution and the solution was extracted with dichloromethane. The organic layer was dried over anhydrous sodium sulfate and the solvent was evaporated under reduced pressure. The residual oil was distilled under reduced pressure to give 700 mg of methyl 2-pyridylmethyl ketone as an oil.

boiling point 140°–145° C. /15 mmHg

NMR (CDCl$_3$): δ 2.24(s, 3H), 3.93(s, 2H), 7.17–7.25(m, 2H), 7.67(dt, 1H), 8.58(d, 1H)

REFERENCE EXAMPLE 8

The following compounds were obtained according to the same procedure as described in Reference Example 7.

(1) Propyl 2-pryidylmethyl ketone, (R-86),

NMR (CDCl$_3$): δ 0.90(t, 3H), 1.63(m, 2H), 2.53(t, 2H), 3.90(s, 2H), 7.17–7.29(m, 2H), 7.66(dt, 1H), 8.56(d, 1H)

(2) Cyclohexylmethyl 2-pyridylmethyl ketone, (R-87),

NMR (CDCl$_3$): δ 0.80–1.96(m, 11H), 2.41(d, 2H), 3.89(s, 2H), 7.15–7.25(m, 2H), 7.65(dt, 1H), 8.56(d, 1H)

(3) Benzyl 2-pyridylmethyl ketone, (R-88),

NMR (CDCl$_3$): δ 3.83(s, 2H), 3.95(s, 2H), 7.13–7.38(m, 7H), 7.63(dt, 1H), 8.57(d, 1H)

(4) 4-Chlorobenzyl 2-pyridylmethyl ketone, (R-89),

NMR (CDCl$_3$): δ 3.80(s, 2H), 3.95(s, 2H), 7.06–7.31(m, 6H), 7.64(dt, 1H), 8.57(d, 1H)

(5) 3-Methylbenzyl 2-pyridylmethyl ketone, (R-90),

NMR(CDCl$_3$): δ 2.32(s, 3H), 3.78(s, 2H), 3.94(s, 2H), 6.97–7.23(m, 6H), 7.63(dt, 1H), 8.56(d, 1H)

(6) 2-Methylbenzyl 2-pyridylmethyl ketone, (R-91),

NMR (CDCl$_3$): δ 2.18(s, 3H), 3.84(s, 2H), 3.93(s, 2H), 7.09–7.20(m, 6H), 7.64(dt, 1H), 8.57(d, 1H)

(7) 4-Methylbenzyl 2-pyridylmethyl ketone, (R-92),

NMR (CDCl$_3$): δ 2.32(s, 3H), 3.78(s, 2H), 3.93(s, 2H), 7.06–7.23(m, 6H), 7.63(dt, 1H), 8.56(d, 1H)

(8) 2,4-Dimethylbenzyl 2-pyridylmethyl ketone, (R-93),

NMR (CDCl$_3$):

δ 2.14(s, 3H), 2.28(s, 3H), 3.80(s, 2H), 3.92(s, 2H), 6.96–7.21(m, 5H), 7.64(dt, 1H), 8.56(d, 1H)

(9) 3,4-Dimethylbenzyl 2-pyridylmethyl ketone, (R-94),

NMR (CDCl$_3$): δ 2.22(s, 6H), 3.76(s, 2H), 3.94(s, 2H), 6.92–7.21(m, 3H), 7.63(dt, 1H), 8.57(d, 1H)

(10) 4-Methoxybenzyl 2-puridylmethyl ketone, (R-95),

NMR (CDCl$_3$): δ 3.76(s, 2H), 3.79(s, 3H), 3.94(s, 2H), 6.86(d, 2H), 7.10(d, 2H), 7.10–7.25(m, 2H), 7.63(dt, 1H), 8.56(d, 1H)

(11) 1-Napthylmethyl 2-pyridylmethyl ketone, (R-96),

NMR (CDCl$_3$): δ 3.93(s, 2H), 4.28(s, 2H), 7.05–7.88(m, 10H), 8.56(d, 1H)

(12) 2-Phenylethyl 2-pyridylmethyl ketone, (R-97),

NMR (CDCl$_3$): δ 2.89(m, 4H), 3.90(s, 2H), 7.13–7.30(m, 7H), 7.63(dt, 1H), 8.55(d, 1H)

(13) 3-Phenylpropyl 2-pyridylmethyl ketone, (R-98),

NMR (CDCl$_3$): δ 1.92(m, 2H), 2.57(m, 4H), 3.87(s, 2H), 7.11–7.30(m, 7H), 7.65(dt, 1H), 8.56(d, 1H)

(14) 2-Pyridylmethyl 3-thienylpropyl ketone, (R-99),

NMR (CDCl$_3$): δ 1.97(m, 2H), 2.60(t, 2H), 2.82(t, 2H), 3.89(s, 2H), 6.74(d, 1H), 6.90(t, 1H), 7.11(d, 1H), 7.15–7.25(m, 2H), 7.66(dt, 1H), 8.56(d, 1H)

(15) 4-Phenylbutyl 2-pyridylmethyl ketone, (R-100),

NMR (CDCl$_3$): δ 1.51–1.69(m, 4H), 2.51–2.69(m, 4H), 3.89(s, 2H), 7.12–7.30(m, 7H), 7.64(dt, 1H), 8.55(d, 1H)

(16) 4-Methyl-2-pyridymethyl 4-phenylbutyl ketone, (R-101),

NMR (CDCl$_3$): δ 1.52–1.70(m, 4H), 2.33(s, 3H), 2.48–2.63(m, 4H), 3.84(s, 2H), 6.97–7.30(m, 7H), 8.39(d, 1H)

(17) 1-Phenyl-4-piperidylmethyl 2-pyridylmethyl ketone, (R-102),

NMR (CDCl$_3$): δ 1.56–2.05(m, 5H), 2.45(d, 2H), 2.81(d, 2H), 3.47(s, 2H), 3.88(s, 2H), 7.14–7.33(m, 7H), 7.65(m, 2H), 8.55(d, 1H)

REFERENCE EXAMPLE 9

Methyl 2-cyano-3,3-dimethylthioacrylate, (R-103),

Sodium methoxide prepared from 4.20 g of sodium and 53 ml of absolute methanol and 5.3 ml of carbon disulfide were added dropwise simultaneously to 9.0 ml of methyl cyanoacetate with occasional cooling to keep a temperature of the reaction mixture below 18° C. The reaction mixture was stirred on an ice-water bath following 30 minutes. Dimethylsulfate (16.5 ml) was added dropwise to the reaction mixture over a period of 30 minutes on an ice water bath, and the stirring was continued following 1 hour at room temperature. Water (125 ml) was added and precipitates were collected by filtration, recrystallized from methanol to give 13.0 g of methyl 2-cyano-3,3-dimethylthioacrylate.

melting point: 85°–86° C.

NMR (CDCl$_3$): δ 2.61(s, 3H), 2.78(s, 3H), 3.48(s, 3H)

REFERENCE EXAMPLE 10

The following compounds were obtained according to the same procedure as that described in Reference Example 11.

(1) Methyl 2-cyano-3,3-dibenzylthioacrylate, (R-104), melting point: 98°–99° C.

NMR (CDCl$_3$): δ 3.83(s, 3H), 4.21(s, 2H), 4.83(s, 2H), 7.20–7.40(m, 10H)

(2) Methyl 2-cyano-3,3-dibutylthioacrylate, (R-105),

NMR (CDCl$_3$): δ 0.94(t, 6H), 1.46(m, 4H), 1.69(m, 4H), 3.13(t, 2H), 3.23(t, 2H), 3.83(s, 3H)

(3) Methyl 2-cyano-3,3-diisopropylthioacrylate, (R-106),

NMR (CDCl$_3$): δ 1.39(d, 12H), 3.83(s, 3H), 3.85–4.05(m, 2H)

(4) Methyl 2-cyano-3,3-dimethallylthioacrylate, (R-107),

NMR (CDCl$_3$): δ 1.81(brs, 6H), 3.51(q, 4H), 3.84(s, 3H), 4.90–5.16(m, 4H)

EXAMPLE 1

Cyclohexylmethyl 3-cyano-2-methylthio-4H-quinolizin-4-one-1-carboxylate, (S-1)

A mixture of 500 mg of cyclohexylmethyl 2-pyridylacetate and 436 mg of methyl 2-cyano-3,3-dimethylthioacrylate was heated for 10 hours at 120° C. The reaction mixture was chromatographed on a silica gel column using a mixed solvent of dichloromethane and diethyl ether (1:1) as an eluent to give 460 mg of cyclohexylmethyl 3-cyano-2-methylthio-4H-quimolizin-4-one-1-carboxylate as pale yellow crystals.

melting point: 130°–133° C.

IR (KBr): 2210, 1705, 1665, 1620 cm$^{-1}$

NMR (CDCl$_3$): δ 1.00–1.85(m, 11H), 2.74(s, 3H), 4.21(d, 2H), 7.29(m, 1H), 7.77(m, 2H), 9.26(d, 1H)

Elementary analysis: C$_{19}$H$_{20}$N$_2$O$_3$S; Calcd.: C, 64.02; H, 5.66; N, 7.86 Found: C, 64.09; H, 5.70; N, 7.15

EXAMPLE 2

The following compounds were obtained according to the same procedure as that described in Example 1.

(1) Cyclopropylmethyl 3-cyano-2-methylthio-4H-quinolizin-4-one-1-carboxylate, (S-2)

melting point: 148°–149° C.

IR (KBr): 2225, 1720, 1660, 1620 cm$^{-1}$

NMR (CDCl$_3$): δ 0.40(m, 2H), 0.67(m, 2H), 1.29(m, 1H), 2.76(s, 3H), 4.25(d, 2H), 7.30(m. 1H), 7.74–7.88(m, 2H), 9.27(d, 1H)

Elementary analysis: C$_{16}$H$_{14}$N$_2$O$_3$S; Calcd.: C, 61.13; H, 4.49; N, 8.91 Found: C, 60.68; H, 4.63; N, 8.64

(2) 3'-Cyclohexylpropyl 3-cyano-2-methylthio-4H-quinolizin-4-one-1-carboxylate (S-3)

melting point: 82°–83° C.

IR (KBr): 2205, 1700, 1662, 1620 cm$^{-1}$

NMR (CDCl$_3$): δ 0.80–1.86(m, 15H), 2.75(s, 3H), 4.38(t, 2H), 7.30(m, 1H), 7.77(m, 2H), 9.26(d, 1H)

Elementary analysis: C$_{21}$H$_{24}$N$_2$O$_3$S; Calcd.: C, 65.60; H, 6.29; N, 7.29 Found: C, 65.42; H, 6.30; N, 7.02

(3) 2',2',2'-Trichloroethyl 3-cyano-2-methylthio-4H-quinolizin-4-one-1-carboxylate, (S-4)

melting point: 138°–140° C.

IR (KBr): 2205, 1730, 1675, 1625 cm$^{-1}$

NMR (CDCl$_3$): δ 2.77(s, 3H), 5.06(s, 2H), 7.33(m, 1H), 7.83(m, 1H), 7.93(d, 1H), 9.30(d, 1H)

Elementary analysis: C$_{14}$H$_9$N$_2$O$_3$SCl$_3$; Calcd.: C, 42.93; H, 2.32; N, 7.15 Found: C, 42.82; H, 2.42; N, 7.25

(4) 2'-Propenyl 3-cyano-2-methylthio-4H-quinolizin-4-one-1-carboxylate, (S-5)

melting point: 70°–72° C.

IR (KBr): 2210, 1700, 1660, 1615 cm$^{-1}$

NMR (CDCl$_3$): δ 2.75(s, 3H), 4.91(dt, 2H), 5.36(dd, 1H), 5.47(m, 1H), 6.00–6.15(m, 1H), 7.30(m, 1H), 7.80(m, 2H), 9.27(d, 1H)

Elementary analysis: C$_{15}$H$_{12}$N$_2$O$_3$S; Calcd.: C, 59.99; H, 4.03; N, 9.33 Found: C, 59.92; H, 4.04; H, 9.04

(5) 2'-Propynl 3-cyano-2-methylthio-4H-quinolizin-4-one-1-carboxylate, (S-6)

melting point: 153°–155° C.

IR (KBr): 2225, 1715, 1660, 1620 cm$^{-1}$

NMR (CDCl$_3$): δ 2.60(t, 1H), 2.76(s, 3H), 5.00(d, 2H), 7.32(m, 1H), 7.81(m, 2H), 9.27(d, 1H)

Elementary analysis: C$_{15}$H$_{10}$N$_2$O$_3$S; Calcd.: C, 60.39; H, 3.38; N, 9.39 Found: C, 60.01; H, 3.31; N, 9.02

(6) Propyl 3-cyano-2-methylthio-4H-quinolizin-4-one-1-carboxylate, (S-7)

Melting point: 71.5°–72.5° C.

IR (KBr): 2210, 1710, 1665, 1620 cm$^{-1}$

NMR (CDCl$_3$): δ 1.04(t, 3H), 1.83(m, 2H), 2.75(s, 3H), 4.37(t, 2H), 7.30(m, 1H), 7.79(m, 2H), 9.26(d, 1H)

Elementary analysis: C$_{15}$H$_{14}$N$_2$O$_3$S; Calcd.: C, 59.59; H, 4.67; N, 9.27 Found: C, 59.37; H, 4.74; N, 9.01

(7) Isopropyl 3-cyano-2-methylthio-4H-quinolizin-4-one-1-carboxylate, (S-8)

melting point: 126.5°–128° C.

IR (KBr): 2210. 1700, 1660, 1615 cm$^{-1}$

NMR (CDCl$_3$): δ 1.43(d, 6H), 2.75(s, 3H), 5.35(m, 1H), 7,29(m, 1H), 7.75(m, 2H), 9.25(d, 1H)

Elementary analysis: C$_{15}$H$_{14}$N$_2$O$_3$S; Calcd.: C, 59.59; H, 4.67; N, 9.27 Found: C, 59.56; H, 4.60; N, 8.75

(8) Butyl 3-cyano-2-methylthio-4H-quinolizin-4-one-1-carboxylate, (S-9)

melting point: 67°–68° C.

IR (KBr): 2220, 1700, 1660, 1615 cm$^{-1}$

NMR (CDCl$_3$): δ 0.98(t, 3H), 1.48(m, 2H), 1.77(m, 2H), 2.75(s, 3H), 4.41(t, 2H), 7.30(m, 1H), 7.78(m, 2H), 9.26(d, 1H)

Elementary analysis: C$_{16}$H$_{16}$N$_2$O$_3$S; Calcd.: C, 60.74; H, 5.10; N, 8.85 Found: C, 60.92; H, 5.05; N, 8.36

(9) 1'-Methylpropyl 3-cyano-2-methylthio-4H-quinolizin-4-one-1-carboxylate, (S-10)

melting point: 75°-76° C.

IR (KBr): 2210, 1710, 1660, 1615 cm$^{-1}$

NMR (CDCl$_3$): δ 0.98(t, 3H), 1.43(d, 3H), 1.76(m, 2H), 2.75(s, 3H), 5.19(m, 1H), 7.30(m, 1H), 7.74(m, 2H), 9.26(d, 1H)

Elementary analysis: C$_{16}$H$_{16}$N$_2$O$_3$S; Calcd.: C, 60.74; H, 5.10; N, 8.85 Found: C, 60.93; H, 5.05; N, 8.12

(10) Isopentyl 3-cyano-2-methylthio-4H-quinolizin-4-one-1-carboxylate, (S-11)

melting point: 65°-67° C.

IR (KBr): 2210, 1695, 1655, 1615 cm$^{-1}$

NMR (CDCl$_3$): δ 0.98(d, 6H), 1.68(m, 2H), 1.78(m, 1H), 2.75(s, 3H), 4.44(t, 2H), 7.30(m, 1H), 7.78(m, 2H), 9.25(d, 1H)

Elementary analysis: C$_{17}$H$_{18}$N$_2$O$_3$S; Calcd.: C, 61.80; H, 5.49; N, 8.48 Found: C, 61.74; H, 5.44; N, 8.19

(11) Cyclopentyl 3-cyano-2-methylthio-4H-quinolizin-4-one-1-carboxylate, (S-12)

melting point: 149°-151° C.

IR (KBr); 2210, 1700, 1660, 1620 cm$^{-1}$

NMR (CDCl$_3$): δ 1.60-2.10(m, 8H), 2.75(s, 3H), 5.50(m, 1H), 7.31)m, 1H), 7.78(m, 2H), 9.26(d, 1H)

Elementary analysis: C$_{17}$H$_{16}$N$_2$O$_3$S; Calcd.: C, 62.18; H, 4.91; N, 8.53 Found: C, 61.83; H, 4.93; N 7.93

(12) Cyclobutyl 3-cyano-2-methylthio-4H-quinolizin-4-one-1-carboxylate, (S-13)

melting point: 111°-112° C.

IR (KBr): 2210, 1700, 1660, 1615 cm$^{-1}$

NMR (CDCl$_3$): δ 1.63-2.60(m, 6H), 2.75(s, 3H), 5.30(m, 1H), 7.30(m, 1H), 7.78(m, 2H), 9.26(d, 1H)

Elementary analysis: C$_{16}$H$_{14}$N$_2$O$_3$S; Calcd.: C, 61.13; H, 4.49; N, 8.91 Found: C, 61.02; H, 4.44; N, 8.24

(13) Cyclohexyl 3-cyano-2-methylthio-4H-quinolizin-4-one-1-carboxylate, (S-14)

melting point: 145°-146° C.

IR (KBr): 2220, 1705, 1660, 1615 cm$^{-1}$

NMR (CDCl$_3$): δ 1.23-2.13(m, 10H), 2.75(s, 3H), 5.12(m, 1H), 7.29(m, 1H), 7.65(m, 2H), 9,26(d, 1H)

Elementary analysis: C$_{18}$H$_{18}$N$_2$O$_3$S; Calcd.: C, 63.14; H, 5.30; N, 8.18 Found: C, 62.95; H, 5.31; N, 8.00

(14) 2'-Cyclohexenyl 3-cyano-2-methylthio-4H-quinolizin-4-one-1-carboxylate, (S-15)

melting point: 143.5°-145° C.

IR (KBr): 2210, 1690, 1660, 1620 cm$^{-1}$

NMR (CDCl$_3$): δ 1.65-2.21(m, 6H), 2.75(s, 3H), 5.59(m, 1H), 5.92(m, 1H), 6.06(m, 1H), 7.29(m, 1H), 7.76(m, 2H), 9.25(d, 1H)

Elementary analysis: C$_{18}$H$_{16}$N$_2$O$_3$S; Calcd.: C, 63.51; H, 4.74; N, 8.23 Found: C, 63.86; H, 4.75; N, 7.76

(15) trans-4'-Hydroxycyclohexyl 3-cyano-2-methylthio-4H-quinolizin-4-one-1-carboxylate, (S-16)

melting point: 169°-170° C.

IR (KBr): 2210, 1700, 1640, 1615 cm$^{-1}$

NMR (CDCl$_3$): δ 1.40-1.75(m. 5H), 1.98-2.28(m, 4H), 2.75(s, 3H), 3.80(m, 1H), 5.12(m, 1H), 7.31(m, 1H), 7.76(m, 2H), 9.26(d, 1H)

Elementary analysis: C$_{18}$H$_{18}$N$_2$O$_4$S; Calcd.: C, 60.32; H, 5.06; N, 7.82 Found: C, 60.37; H, 5.03 N, 7.85

(16) 2'-Methylcyclohexyl 3-cyano-2-methylthio-4H-quinolizin-4-one-1-carboxylate, (S-17)

melting point: 105°-108° C.

IR (KBr): 2205, 1720, 1665, 1620 cm$^{-1}$

NMR (CDCl$_3$): δ 0.99 and 1.03(d, 3H), 1.10-2.37(m, 9H), 2.75(s, 3H), 4.78 and 5.31(m, 1H), 7.31(dd, 1H), 7.75(m, 2H), 9.26(d, 1H)

Elementary analysis: C$_{19}$H$_{20}$N$_2$O$_3$S; Calcd.: C, 64.02 H, 5.56; N, 7.86 Found: C, 63.97; H, 5.68; N, 7.74

(17) Cyclohexyl 3-cyano-8-methyl-2-methylthio-4H-quinolizin-4-one-1-carboxylate, (S-18)

melting point: 179°-180° C.

IR (KBr): 2200, 1720, 1670, 1630 cm$^{-1}$

NMR (CDCl$_3$): δ 1.23-2.15(m, 10H), 2.52(brs, 3 2.72(s, 3H), 5.13(m, 1H), 7.13(dd, 1H), 7.26(brs, 1h$_y$, 9.16(d, 1H)

Elementary analysis: C$_{19}$H$_{20}$N$_2$O$_3$S; Calcd.: C, 64.02; H, 5.66; N, 7.86 Found: C, 64.06; H, 5.60; N, 7.76

(18) Cycloheptyl 3-cyano-2-methylthio-4H-quinolizin-4-one-1-carboxylate, (S-19)

melting point: 130°-131° C.

IR (KBr): 2210, 1700, 1660, 1620 cm$^{-1}$

NMR (CDCl$_3$): δ 1.50-2.20(m, 12H), 2.75(s, 3H), 5.30(m, 1H), 7.30(m, 1H), 7.76(m, 2H), 9.25(m, 1H)

Elementary analysis: C$_{19}$H$_{20}$N$_2$O$_3$S; Calcd.: C, 64.02; H, 5.66; N, 7.86 Found: C, 63.93; H, 5.66; N, 7.63

(19) Cyclooctyl 3-cyano-2-methylthio-4H-quinolizin-4-one-1-carboxylate, (S-20)

melting point: 121.5°-122.5° C.

IR (KBr): 2205, 1700, 1660, 1620 cm$^{-1}$

NMR (CDCl$_3$): δ 1.45-2.10(m, 14H), 2.75(s, 3H), 5.28(m, 1H), 7.30(m, 1H), 7.74(m, 2H), 9.25(d, 1H)

Elementary analysis: C$_{20}$H$_{22}$N$_2$O$_3$S; Calcd.: C, 64.84; H, 5.99; N, 7.56 Found: C, 64.41; H, 5.95; N, 7.54

(20) 2'-Adamantyl 3-cyano-2-methylthio-4H-quinolizin-4-one-1-carboxylate, (S-21)

melting point: 177°-178° C.

IR (KBr): 2205, 1705, 1670, 1615 cm$^{-1}$

NMR (CDCl$_3$): δ 1.58-2.28(m, 14H), 2.75(s, 3H), 5.32(m, 1H), 7.30(m, 1H), 7.75(m, 2H), 9.26(d, 1H)

Elementary analysis: C$_{22}$H$_{22}$N$_2$O$_3$S; Calcd.: C, 66.98; H, 5.62; N, 7.10 Found: C, 67.54; H, 5.68; N, 6.32

(21) 1',2',3',4'-Tetrahydro-1'-naphthyl 3-cyano-2-methylthio-4H-quinolizin-4-one-1-carboxylate, (S-22)

amorphous powder

IR (KBr): 2205, 1715, 1670, 1620 cm$^{-1}$

NMR (CDCl$_3$): δ 1.70-2.40(m, 4H), 2.70(s, 3H), 2.71-2.95(m, 2H), 6.37(t, 1H), 7.08-7.32(m, 4H), 7.46(m, 1H), 7.70(m, 2H), 9.24(d, 1H)

Elementary analysis: C$_{22}$H$_{18}$N$_2$O$_3$S; Calcd.: C, 67.68; H, 4.65; N, 7.18 Found: C, 67.50; H, 4.55; N, 7.08

(22) 4'-Bromobenzyl 3-cyano-2-methylthio-4H-quinolizin-4-one-1-carboxylate, (S-23)

melting point: 119.5°-120° C.

IR (KBr): 2210, 1720, 1670, 1625 cm$^{-1}$

NMR (CDCl$_3$): δ 2.69(s, 3H), 5.37(s, 2H), 7.29(m, 1H), 7.34(d, 2H), 7.53(d, 2H), 7.72(m, 2H), 9.25(d, 1H)

Elementary analysis: C$_{19}$H$_{13}$N$_2$O$_3$S; Calcd.: C, 53.16; H, 3.05; N, 6.53 Found: C, 53.08; H, 2.90; N, 6.33

(23) 1'-Phenylethyl 3-cyano-2-methylthio-4H-quinolizin-4-one-1-carboxylate, (S-24)

melting point: 116.5°-118° C.

IR (KBr): 2200, 1710, 1670, 1625 cm$^{-1}$

NMR (CDCl$_3$): δ 1.74(d, 3H), 2.67(s, 3H), 6.21(q, 1H), 7.23-7.70(m, 8H), 9.23(d, 1H)

Elementary analysis: C$_{20}$H$_{16}$N$_2$O$_3$S; Calcd.: C, 65.92; H, 4.43; N, 7.69 Found: C, 65.55; H, 4.33; N, 7.65

(24) 3',4'-Dimethylbenzyl 3-cyano-2-methylthio-4H-quinolizin-4-one-1-carboxylate, (S-25)

melting point: 123.5°-125° C.

IR (KBr): 2210, 1705, 1670, 1625 cm$^{-1}$

NMR (CDCl$_3$): δ 2.28(brs, 6H), 2.69(s, 3H), 5.37(s, 2H), 7.13-7.30(m, 4H), 7.71(m, 2H), 9.24(d, 1H)

Elementary analysis: $C_{21}H_{18}N_2O_3S$; Calcd.: C, 66.65; H, 4.79; N, 7.40 Found: C, 66.50; H, 4.75; N, 6.92

(25) Piperonyl 3-cyano-2-methylthio-4H-quinolizin-4-one-1-carboxylate, (S-26)
melting point: 173°–175.5° C.
IR (KBr): 2210, 1730, 1675, 1630 cm$^{-1}$
NMR (CDCl$_3$): δ 2.70(s, 3H), 5.32(s, 2H), 5.99(s, 2H), 6.90(d, 1H), 6.95(m, 2H), 7.28(m, 1H), 7.73(d, 2H), 9.24(d, 1H)
Elementary analysis: $C_{20}H_{14}N_2O_5S$; Calcd.: C, 60.91; H, 3.58; N, 7.10 Found: C, 61.13; H, 3.54; N, 7.30

(26) 3',4',5'-Trimethoxybenzyl 3-cyano-2-methylthio-4H-quinolizin-4-one-1-carboxylate, (S-27)
melting point: 140°–142° C.
IR (KBr): 2210, 1705, 1675, 1625 cm$^{-1}$
NMR (CDCl$_3$): δ 2.71(s, 3H), 3.86(s, 3H), 3.87(s, 6H), 5.37(s, 2H), 6.69(s, 2H), 7.30(m, 1H), 7.72(m, 2H), 9.25(d, 1H)
Elementary analysis: $C_{22}H_{20}N_2O_6S$; Calcd.: C, 59.99; H, 4.58; N, 6.36 Found: C, 60.27; H, 4.55; N, 6.14

(27) Benzyl 3-cyano-8-menthyl-2-methylthio-4H-quinolizin-4-one-1-carboxylate, (S-28)
melting point: 177°–179° C.
IR (KBr): 2200, 1725, 1665, 1630 cm$^{-1}$
NMR (CDCl$_3$): δ 2.42(s, 3H), 2.67(s, 3H), 5.44(s, 2H), 7.10(dd, 1H), 7.26(brs, 1H), 7.34–7.51(m, 5H), 9.13(d, 1H)
Elementary analysis: $C_{20}H_{16}N_2O_3S$; Calcd.: C, 65.92; H, 4.43; N, 7.69 Found: C, 65.64; H, 4.52; N, 7.48

(28) Benzyl 3-cyano-2-methylthio-4H-quinolizin-4-one-1-carboxylate, (S-29)
melting point: 95°–97° C.
IR (KBr): 2210, 1715, 1660, 1615 cm$^{-1}$
NMR (CDCl$_3$): δ 2.68(s, 3H), 5.44(s, 2H), 7.30(m, 1H), 7.37–7.50(m, 5H), 7.71(m, 2H), 9.24(m, 1H)
Elementary analysis: $C_{19}H_{14}N_2O_3S$; Calcd.: C, 65.13; H, 4.03; N, 7.99 Found: C, 65.15; H, 3.98; N, 7.59

(29) 1'-(4-Bromophenyl)ethyl 3-cyano-2-methylthio-4H-quinolizin-4-one-1-carboxylate, (S-30)
melting point: 142°–144° C.
IR (KBr): 2200, 1735, 1665, 1620 cm$^{-1}$
NMR (CDCl$_3$): δ 1.71(d, 3H), 2.69(s, 3H), 6.15(q, 1H), 7.28–7.57(m, 6H), 7.70(dt, 1H), 9.24(d, 1H)
Elementary analysis: $C_{20}H_{15}N_2O_3S$; Calcd.: C, 54.19 H, 3.41; N, 6.32 Found: C, 54.21; H, 3.42; N, 6.24

(30) 4'-Methoxybenzyl 3-cyano-2-methylthio-4H-quinolizin-4-one-1-carboxylate, (S-31)
melting point: 105°–106° C.
IR (KBr): 2205, 1700, 1660, 1620 cm$^{-1}$
NMR (CDCl$_3$): δ 2.68(s, 3H), 3.83(s, 3H), 5.37(s, 2H), 6.93(d, 2H), 7.27(m, 1H), 7.39(d, 2H), 7.69(m, 2H), 9.23(d, 1H)
Elementary analysis: $C_{20}H_{16}N_2O_4S$; Calcd.: C, 63.15; H, 4.24; N, 7.36 Found: C, 63.15; H, 4.18; N, 7.56

(31) 1'-(4-Cyanophenyl)ethyl 3-cyano-2-methylthio-4H-quinolizin-4-one-1-carboxylate, (S-32)
melting point: 154°–156° C.
IR (KBr): 2210, 1735, 1665, 1620 cm$^{-1}$
NMR (CDCl$_3$): δ 1.74(d, 3H), 2.71(s, 3H), 6.19(q, 1H), 7.31(dd, 1H), 7.53–7.77(m, 6H), 9.26(d, 1H)
Elementary analysis: $C_{21}H_{15}N_3O_3S$; Calcd.: C, 64.77; H, 3.88; N, 10.79 Found: C, 64.56; H, 3.62; N, 10.87

(32) 4'-Ethoxybenzyl 3-cyano-2-methylthio-4H-quinolizin-4-one-1-carboxylate, (S-33)
melting point: 126°–127° C.
IR (KBr): 2200, 1710, 1670, 1625 cm$^{-1}$
NMR (CDCl$_3$): δ 1.42(t, 3H), 2.68(s, 3H), 4.05(q, 2H), 5.36(s, 2H), 6.92(d, 2H), 7.26(m, 1H), 7.38(d, 2H), 7.68(m., 2H), 9.23(d, 1H)
Elementary analysis: $C_{21}H_{18}N_2O_4S$; Calcd.: C, 63.95; H, 4.60; N, 7.10 Found: C, 64.23; H, 4.75; N, 6.78

(33) 4'-Fluorobenzyl 3-cyano-2-methylthio-4H-quinolizin-4-one-1-carboxylate, (S-34)
melting point: 164°–165° C.
IR (KBr): 2200, 1665, 1625 cm$^{-1}$
NMR (CDCl$_3$): δ 2.68(s, 3H), 5.39(s, 2H), 7.09(t, 2H), 7.29(m, 1H), 7.46(m, 2H), 7.70(m, 2H), 9.24(d, 1H)
Elementary analysis: $C_{19}H_{13}N_2O_3SF$; Calcd.: C 61.95; H, 3.56; N, 7.60 Found: C, 61.85; H, 3.46; N, 7.50

(34) 3'-Methoxybenzyl 3-cyano-2-methylthio-4H-quinolizin-4-one-1-carboxylate, (S-35)
melting point: 50.5°–51° C.
IR (KBr): 2200, 1715, 1660, 1625 cm$^{-1}$
NMR (CDCl$_3$): δ 2.70(s, 3H), 3.82(s, 3H), 5.41(s, 2H), 6.91(dd, 1H), 6.99–7.07(m, 2H), 7.26–7.37(m, 2H), 7.72(m, 2H), 9.24(d, 1H)
Elementary analysis: $C_{20}H_{16}N_2O_4S$; Calcd.: C, 63.15; H, 4.24; N, 7.36 Found: C, 63.21; H, 4.43; N, 7.01

(35) 4'-Isopropylbenzyl 3-cyano-2-methylthio-4H-quinolizin-4-one-1-carboxylate, (S-36)
melting point: 154.5°–155° C.
IR (KBr): 2200, 1710, 1670, 1625 cm$^{-1}$
NMR (CDCl$_3$): δ 1.25(d, 6H), 2.68(s, 3H), 2.93(m, 1H), 5.40(s, 2H), 7.24–7.30(m, 3H), 7.39(d, 2H), 7.69(m, 2H), 9.24(d, 1H)
Elementary analysis: $C_{22}H_{20}N_2O_3S$; Calcd.: C, 67.33; H, 5.14; N, 7.14 Found: C, 67.32; H, 5.09; N, 6.96

(36) 2'-Methoxybenzyl 3-cyano-2-methylthio-4H-quinolizin-4-one-1-carboxylate, (S-37)
melting point: 131.7°–132.5° C.
IR (KBr): 2200, 1720, 1670, 1625 cm$^{-1}$
NMR (CDCl$_3$): δ 2.68(s, 3H), 3.88(s, 3H), 5.49(s, 2H), 6.91–7.00(m, 2H), 7.24–7.44(m, 3H), 7.67–7.80(m, 2H), 9.23(d, 1H)
Elementary analysis: $C_{20}H_{16}N_2O_4S$; Calcd.: C, 63.15; H, 4.24; N, 7.36 Found: C, 62.95; H, 4.17; N, 7.22

(37) 3'-Chlorobenzyl 3-cyano-2-methylthio-4H-quinolizin-4-one-1-carboxylate, (S-38)
melting point: 96°–98° C.
IR (KBr): 2210, 1705, 1675, 1625 cm$^{-1}$
NMR (CDCl$_3$): δ 2.71(s, 3H), 5.40(s, 2H), 7.26–7.35(m, 4H), 7.46(s, 1H), 7.70–7.79(m, 2H), 9.25(d, 1H)
Elementary analysis: $C_{19}H_{13}N_2O_3SCl$; Calcd.: C, 59.30; H, 3.40; N, 7.28 Found: C, 59.30; H, 3.38; N, 7.05

(38) 2'-Chlorobenzyl 3-cyano-2-methylthio-4H-quinolizin-4-one-1-carboxylate, (S-39)
melting point: 145°–146° C.
IR (KBr): 2205, 1715, 1675, 1625 cm$^{-1}$
NMR (CDCl$_3$): δ 2.70(s, 3H), 5.55(s, 2H), 7.26–7.36(m, 3H), 7.42(m, 1H), 7.54(m, 1H), 7.78(m, 2H), 9.25(d, 1H)
Elementary analysis: $C_{19}H_{13}N_2O_3SCl$; Calcd.: C, 59.30; H, 3.40; N, 7.28 Found: C, 58.93; H, 3.41; N, 7.04

(39) 4'-phenylbenzyl 3-cyano-2-methylthio-4H-quinolizin-4-one-1-carboxylate, (S-40)
melting point: 143°–145° C.
IR (KBr): 2205, 1710, 1670, 1625 cm$^{-1}$
NMR (CDCl$_3$): δ 2.71(s, 3H), 5.48(s, 2H), 7.26–7.75(m, 12H), 9.24(d, 1H)
Elementary analysis: $C_{25}H_{18}N_2O_3S$; Calcd.: C, 70.41; H, 4.25; N, 6.57 Found: C, 70.48; H, 4.03; N, 6.27

(40) 2'-Napthylmethyl 3-cyano-2-methylthio-4H-quinolizin-4-one-1-carboxylate, (S-41)
melting point: 124.8°–125.5° C.
IR (KBr): 2210, 1715, 1670, 1625 cm$^{-1}$
NMR (CDCl$_3$): δ 2.69(s, 3H), 5.60(s, 2H), 7.26(m, 1H), 7.50–7.97(m, 9H), 9.24(d, 1H)

(41) 1'-Naphthylmethyl 3-cyano-2-methylthio-4H-quinolizin-4-one-1-carboxylate, (S-42)
amorphous powder
IR (KBr): 2205, 1720, 1670, 1625 cm$^{-1}$
NMR (CDCl$_3$): δ 2.60(s, 3H), 5.91(s, 2H), 7.24(m, 1H), 7.47–7.62(m, 5H), 7.68(d, 1H), 7.91(m, 2H), 8.14(m, 1H), 9.21(d, 1H)
Elementary analysis: C$_{23}$H$_{16}$N$_2$O$_3$S; Calcd.: C, 68.99; H, 4.03; N, 7.00 Found: C, 68.89; H, 3.93; N, 6.90

(42) 1'-Methyl-2'-phenylethyl 3-cyano-2-methylthio-4H-quinolizin-4-one-1-carboxylate, (S-43)
melting point: 120°–122.5° C.
IR (KBr): 2210, 1720, 1670, 1625 cm$^{-1}$
NMR (CDCl$_3$): δ 1.50(d, 3H), 2.69(s, 3H), 3.00(d, 2H), 5.60(m, 1H), 6.92(d, 1H), 7.19–7.36(m, 6H), 7.49(dt, 1H), 9.20(d, 1H)
Elementary analysis: C$_{21}$H$_{18}$N$_2$O$_3$S; Calcd.: C, 66.65; H, 4.79; N, 7.40 Found: C, 66.47; H, 4.69; N, 6.97

(43) 2',2'-Diphenylethyl 3-cyano-2-methylthio-4H-quinolizin-4-one-1-carboxylate, (S-44)
melting point: 144°–145.5° C.
IR (KBr): 2210, 1725, 1700, 1670, 1620 cm$^{-1}$
NMR (CDCl$_3$): δ 2.61(s, 3H), 4.54(t, 1H), 5.01(d, 2H), 7.10(d, 1H), 7.18–7.40(m, 11H), 7.45(m, 1H), 9.18(d, 1H)
Elementary analysis: C$_{26}$H$_{20}$N$_2$O$_3$S; Calcd.: C, 70.89; H, 4.58; N, 6.36 Found: C, 71.34; H, 4.56; N, 5.78

(44) 3'-Phenylpropyl 3-cyano-2-methylthio-4H-quinolizin-4-one-1-carboxylate, (S-45)
melting point: 80°–81° C.
IR (KBr): 2200, 1700, 1665, 1620 cm$^{-1}$
NMR (CDCl$_3$): δ 2.13(m, 2H), 2.75(s, 3H), 2.78(t, 2H), 4.43(t, 2H), 7.18–7.36(m, 6H), 7.77(m, 2H), 9.26(d, 1H)
Elementary analysis: C$_{21}$H$_{18}$N$_2$O$_3$S; Calcd.: C, 66.65; H, 4.79; N, 7.40 Found: C, 66.93; H, 4.72; N, 6.92

(45) 1'-Methyl-3'-phenylpropyl 3-cyano-2-methylthio-4H-quinolizin-4-one-1-carboxylate, (S-46)
amorphous powder
IR (KBr): 2210, 1715, 1670, 1630 cm$^{-1}$
NMR (CDCl$_3$): δ 1.48(d, 3H), 2.05(m, 2H), 2.76(s, 3H), 2.65–2.85(m, 2H), 5.30(q, 1H), 7.17–7.35(m, 6H), 7.75(m, 2H), 9.21(d, 1H)
Elementary analysis: C$_{22}$H$_{20}$N$_2$O$_3$S; Calcd.: C, 67.33; H, 5.14; N, 7.14 Found: C, 67.23; H, 5.04; N, 7.04

(46) trans-Cinnamyl 3-cyano-2-methylthio-4H-quinolizin-4-one-1-carboxylate, (S-47)
melting point: 124°–125° C.
IR (KBr): 2200, 1710, 1665, 1620 cm$^{-1}$
NMR (CDCl$_3$): δ 2.74(s, 3H), 5.06(dd, 2H), 6.41(dt, 1H), 6.80(d, 1H), J=16 Hz), 7.27–7.45(m, 6H), 7.73–7.87(m, 2H), 9.25(d, 1H)
Elementary analysis: C$_{21}$H$_{16}$N$_2$O$_3$S; Calcd.: C, 67.01; H, 4.28; N, 7.44 Found: C, 66.91; H, 4.20; N, 6.96

(47) 2'-Phenylethyl 3-cyano-2-methylthio-4H-quinolizin-4-one-1-carboxylate, (S-48)
melting point: 67°–69° C.
IR (KBr): 2220, 1700, 1660, 1615 cm$^{-1}$
NMR (CDCl$_3$): δ 2.67(s, 3H), 3.12(t, 2H), 4.68(t, 2H), 7.23–7.38(m, 6H), 7.42(d, 1H), 7.60(dt, 1H), 9.22(d, 1H)
Elementary analysis: C$_{20}$H$_{16}$N$_2$O$_3$S; Calcd.: C, 65.92; H, 4.43; N, 7.69 Found: C, 66.00; H, 4.33; N, 7.35

(48) 4'-Phenylbutyl 3-cyano-2-methylthio-4H-quinolizin-4-one-1-carboxylate, (S-49)
melting point: 70°–72° C.
IR (KBr): 2210, 1710, 1670, 1620 cm$^{-1}$
NMR (CDCl$_3$): δ 1.72–1.90(m, 4H), 2.69(t, 2H), 2.71(s, 3H), 4.42(t, 2H), 7.15–7.33(m, 6H), 7.75(m, 2H), 9.26(d, 1H)
Elementary analysis: C$_{22}$H$_{20}$N$_2$O$_3$S; Calcd.: C, 67.33; H, 5.14; N, 7.14 Found: C, 67.02; H, 5.12; N, 6.72

(49) 2'-Phenylethyl 3-cyano-8-methyl-2-methylthio-4H-quinolizin-4-one-1-carboxylate, (S-50)
melting point: 134°–136° C.
IR (KBr): 2210, 1710, 1670, 1635 cm$^{-1}$
NMR (CDCl$_3$): δ 2.43(s, 3H), 2.65(s, 3H), 3.12(t, 2H), 4.66(t, 2H), 7.10(dd, 1H), 7.22–7.37(m, 6H), 9.14(d, 1H)
Elementary analysis: C$_{21}$H$_{18}$N$_2$O$_3$S; Calcd.: C, 66.65; H, 4.79; N, 7.40 Found: C, 66.77; H, 4.75; N, 7.25

(50) 3'-Phenylpropyl 3-cyano-8methyl-2-methylthio-4H-quinolizin-4-one-1-carboxylate, (S-51)
melting point: 119°–120° C.
IR (KBr): 2200, 1720, 1670, 1635 cm$^{-1}$
NMR (CDCl$_3$): δ 2.13(m, 2H), 2.52(s, 3H), 2.73(s, 3H), 2.79(t, 2H), 4.43(t, 2H), 7.13–7.36(m, 6H), 7.53(brs, 1H), 9.16(d, 1H)
Elementary analysis: C$_{22}$H$_{20}$N$_2$O$_3$S; Calcd.: C, 67.33; H, 5.14; N, 7.14 Found: C, 67.42; H, 5.10; N, 6.97

(51) 3'-Phenylpropyl 3-cyano-2-ethylthio-4H-quinolizin-4-one-1-carboxylate, (S-52)
melting point: 50°–51° C.
IR (KBr): 2210, 1695, 1670, 1620 cm$^{-1}$
NMR (CDCl$_3$): δ 1.32(t, 3H), 2.13(m, 2H), 2.79(t, 2H), 3.29(q, 2H), 4.43(t, 2H), 7.15–7.35(m, 6H), 7.75(m, 2H), 9.28(d, 1H)
Elementary analysis: C$_{22}$H$_{20}$N$_2$O$_3$S; Calcd.: C, 67.33; H, 5.14; N, 7.14 Found: C, 67.25; H, 5.15; N, 6.84

(52) 2'-(4-Chorophenoxy)ethyl 3-cyano-2-methylthio-4H-quinolizin-4-one-1-carboxylate, (S-53)
melting point: 136°–138° C.
IR (KBr): 2210, 1730, 1670, 1625 cm$^{-1}$
NMR (CDCl$_3$): δ 2.71(s, 3H), 4.31(t, 2H), 4.77(t, 2H), 6.85(d, 2H), 7.22–7.34(m, 3H), 7.71(dt, 1H), 7.85(d, 1H), 9.25(d, 1H)
Elementary analysis: C$_{20}$H$_{15}$N$_2$O$_4$SCl; Calcd.: C, 57.90; H, 3.64; N, 6.75 Found: C, 57.70; H, 3.60; N, 6.79

(53) 3'-Phenoxypropyl 3-cyano-2-methylthio-4H-quinolizin-4-one-1-carboxylate, (S-54)
melting point: 100°–102° C.
IR (KBr): 2210, 1720, 1670, 1625 cm$^{-1}$
NMR (CDCl$_3$): δ 2.27(m, 2H), 2.65(s, 3H), 4.13(t, 2H), 4.63(t, 2H), 6.91(d, 2H), 6.97(t, 1H), 7.23–7.35(m, 3H), 7.56(dt, 1H), 7.73(d, 1H), 9.23(d, 1H)
Elementary analysis: C$_{21}$H$_{18}$N$_2$O$_4$S; Calcd.: C, 63.94; H, 4.60; N, 7.10 Found: C, 63.66; H, 4.48; N, 7.01

(54) 2'-Phenylthioethyl 3-cyano-2-methylthio-4H-quinolizin-4-one-1-carboxylate, (S-55)
melting point: 82°–84° C.
IR (KBr): 2210, 1700, 1660, 1620 cm$^{-1}$
NMR (CDCl$_3$): δ 2.74(s, 3H), 3.31(t, 2H), 4.57(t, 2H), 7.18–7.37(m, 4H), 7.42(d, 2H), 7.76(dt, 1H), 7.86(d, 1H), 9.25(d, 1H)
Elementary analysis: C$_{20}$H$_{16}$N$_2$O$_3$S$_2$; Calcd.: C, 60.59; H, 4.07; N, 7.07 Found: C, 60.49; H, 4.07; N, 7.18

(55) Ethyl 3-cyano-2-methylthio-4H-quinolizin-4-one-1-carboxylate, (S-56)
melting point: 90°–92° C.
IR (KBr): 2210, 1720, 1670, 1620 cm$^{-1}$
NMR (CDCl$_3$): δ 1.44(t, 3H), 1.81(brs, 3H), 3.87(brs, 2H), 4.48(q, 2H), 4.81(m, 1H), 4.91(m, 1H), 7.31(m, 1H), 7.76(m, 2H), 9.27(d, 1H)
Elementary analysis: C$_{17}$H$_{16}$N$_2$O$_3$S; Calcd.: C, 62.19; H, 4.91; N, 8.53 Found: C, 62.30; H, 5.12; N, 8.49

(56) Ethyl 3-cyano-2-isopropylthio-4H-quinolizin-4-one-1-carboxylate, (S-57)

melting point: 103°–105°C.
IR (KBr): 2210, 1720, 1660, 1620 cm$^{-1}$
NMR (CDCl$_3$): δ 1.34(d, 6H), 1.44(t, 3H), 4.06(m, 1H), 4.80(q, 2H), 7.32(m, 1H), 7.70–7.85(m, 2H), 9.28(d, 1H)
Elementary analysis: C$_{16}$H$_{16}$N$_2$O$_3$S; Calcd.: C, 60.75; H, 5.10; N, 8.86 Found: C, 60.70; H, 5.12; N, 8.83

(57) Ethyl 3-cyano-2-butylthio-4H-quinolizin-4-one-1-carboxylate, (S-58)
melting point: 58°–61° C.
IR (KBr): 2225, 1715, 1660, 1620 cm$^{-1}$
NMR (CDCl$_3$): δ 0.90(t, 3H), 1.43(m, 5H), 1.59(m, 2H), 3.25(t, 2H), 4.48(q, 2H), 7.31(m, 1H), 7.75(m, 2H), 9.26(d, 1H).
Elementary analysis: C$_{17}$H$_{18}$N$_2$O$_3$S; Calcd.: C, 61.81; H, 5.49; N, 8.48 Found: C, 61.75; H, 5.53; N, 8.42

(58) Ethyl 3-cyano-2-benzylthio-4H-quinolizin-4-one-1-carboxylate, (S-59)
melting point: 143°–144° C.
IR (KBr): 2215, 1720, 1670, 1620 cm$^{-1}$
NMR (CDCl$_3$): δ 1.40(t, 3H), 4.44(q, 2H), 4.45(brs, 2H), 7.18–7.39(m, 6H), 7.75(m, 2H), 9.26(d, 1H),
Elementary analysis: C$_{20}$H$_{16}$N$_2$O$_3$S; Calcd.: C, 65.60; H, 6.29; N, 7.29 Found: C, 65.42; H, 6.30; N, 7.02

EXAMPLE 3

3-Cyano-N,N-dibenzyl-2-methylthio-4H-quinolizin-4-one-1-carboxamide, (S-60)

A mixture of 486 mg of N,N-dibenzyl-2-pyridylacetamide and 312 mg of methyl 2-cyano-3,3-dimethylthioacrylate was heated at 120° C. for 10 hours. The reaction mixture was chromatographed on a silica gel column using a mixed solvent of dichloromethane, diethyl ether and methanol (1:1:0.2) as an eluent to give 260 mg of 3-cyano-N,N-dibenzyl-2-methylthio-4H-quinolizin-4-one-1-carboxamide as pale yellow crystals.
melting point: 85–87° C.
IR (KBr): 2210, 1660, 1620 cm$^{-1}$
NMR (CDCl$_3$): δ 2.74(s, 3H), 4.29(s, 2H), 4.65(d, 1H), 5.09(d, 1H), 6.88(m, 2H), 7.12–7.23(m, 4H), 7.36–7.50(m, 6H), 7.57(dt, 1H), 9.15(d, 1H)
Elementary analysis: C$_{26}$H$_{21}$N$_3$O$_2$S; Calcd.: C, 71.05; H, 4.82: N, 9.56 Found: C, 70.66; H, 4.73; N, 9.46

EXAMPLE 4

The following compounds were obtained according to the same procedure as that described in Example 3.

(1) 3-Cyano-N,N-dicyclohexyl-2-methylthio-4H-quinolizin-4-one-1-carboxamide, (S-61)
melting point: 268–271° C.
IR (KBr): 2210, 1660, 1620 cm$^{-1}$
NMR (CDCl$_3$): δ0.83–2.07(m, 18H), 2.60–2.88(m, 2H), 2.77(s, 3H), 3.16(m, 2H), 7.24(dd, 1H), 7.54(d, 1H), 7.68(dt, 1H), 9.23(d, 1H)
Elementary analysis: C$_{24}$H$_{29}$N$_3$O$_2$S; Calcd.: C, 68.05; H, 6.90; N, 9.92 Found: C, 68.36; H, 6.96; N, 9.84

(2) 3-Cyano-N,N-diethyl-2-methylthio-4H-quinolizin-4-one-1-carboxamide, (S-62)
melting point: 170.5–171.5° C.
IR (KBr): 2210, 1660, 1620 cm$^{-1}$
NMR (DMSO-d$_6$): δ 1.07(t, 3H), 1.36(t, 3H), 2.78(s, 3H), 3.30(q, 2H), 3.68(m, 2H), 7.60–7.71(m, 2H), 8.16(dt, 1H), 9.28(d, 1H)
Elementary analysis: C$_{16}$H$_{17}$N$_3$O$_2$S; Calcd.: C, 60.93; H, 5.43; N, 13.32 Found: C, 60.85; H, 5.49; N, 13.00

(3) 3-Cyano-N,N-diisopropyl-2-methylthio-4H-quinolizin-4-one-1-carboxamide, (S-63)
melting point: 241–242.5° C.
IR (KBr): 2210, 1660, 1620 cm$^{-1}$
NMR (CDCl$_3$): δ 1.03(d, 3H), 1.28(d, 3H), 1.63(d, 3H), 1.66(d, 3H), 2.79(s, 3H), 3.55–3.71(m, 2H), 7.25(dt, 1H), 7.53(d, 1H), 7.70(dt, 1H), 9.23(d, 1H)
Elementary analysis: C$_{18}$H$_{21}$N$_3$O$_2$S; Calcd.: C, 62.95; H, 6.16; N, 12.23 Found: C, 62.77; H, 6.16; N, 11.96

(4) 3-Cyano-N,N-diisobutyl-2-methylthio-4H-quinolizin-4-one-1-carboxamide, (S-64)
melting point: 167° C.
IR (KBr): 2200, 1660, 1610 cm$^{-1}$
NMR (CDCl$_3$): δ 0.61(d, 3H), 0.80(d, 3H), 1.06(d, 3H), 1.07(d, 3H), 1.75(m, 1H), 2.22(m, 1H), 2.91(dd, 1H), 2.76(s, 3H), 3.00–3.13(m, 2H), 3.87(dd, 1H), 7.28(dd, 1H), 7.59(d, 1H), 7.71(dt, 1H), 9.25(d, 1H)
Elementary analysis: C$_{20}$H$_{25}$N$_3$O$_2$; Calcd.: C, 64.66; H, 6.78; N, 11.31 Found: C, 64.54; H, 6.80; N, 11.28

(5) 3-Cyano-N,N-dihexyl-2-methylthio-4H-quinolizin-4-one-1-carboxamide, (S-65)
melting point: 94–95° C.
IR (KBr): 2210, 1665, 1625 cm$^{-1}$
NMR (CDCl$_3$): δ 0.73(t, 3H), 0.93(t, 3H), 1.00–1.83(m, 16H), 2.77(s, 3H), 3.10(t, 2H), 3.43(m, 1H), 3.74(m, 1H), 7.29(dd, 1H), 7.52(d, 1H), 7.70(dt, 1H), 9.24(d, 1H)
Elementary analysis: C$_{24}$H$_{33}$N$_3$O$_2$S; Calcd.: C, 67.41; H, 7.78; N, 9.83 Found: C, 66.85; H, 8.00; N, 9.71

(6) N-Benzyl-3-cyano-N-methyl-2-methylthio-4H-quinolizin-4-one-1-carboxamide, (S-66)
melting point: 191–193° C.
IR (KBr): 2210, 1680, 1625 cm$^{-1}$
NMR (CDCl$_3$): δ 2.77(s, 3H), 2.80(m, 3H), 4.82(d, 1H), 4.88(d, 1H), 7.20–7.53(m, 7H), 7.69(dt, 1H), 9.24(d, 1H)
Elementary analysis: C$_{20}$H$_{17}$N$_3$O$_2$S; Calcd.: C, 66.10; H, 4.71; N, 11.56 Found: C, 65.83; H, 4.59; N, 11.10

(7) 3-Cyano-2-methylthio-N-phenyl-N-(2-phenylaminoethyl)-4H-quinolizin-4-one-1-carboxamide, (S-67)
melting point: 65–75° C.
IR (KBr): 2200, 1660, 1620 cm$^{-1}$
NMR (CDCl$_3$): δ 2.69(s, 3H), 3.45(m, 2H), 3.93(dt, 1H), 4.62(m, 1H), 6.66(d, 2H), 6.78(t, 1H), 7.04–7.25(m, 9H), 7.57(dt, 1H), 7.82(d, 1H), 9.07(d, 1H)
Elementary analysis: C$_{26}$H$_{22}$N$_4$O$_2$S; Calcd.: C, 68.70; H, 4.88; N, 12.33 Found: C, 68.50; H, 4.77; N, 12.11

(8) N-Benzyl-3-cyano-N-isopropyl-2-methylthio-4H-quinolizin-4-one-1-carboxamide (S-68)
melting point: 220–223° C.
IR (KBr): 2210, 1675, 1620 cm$^{-1}$
NMR (CDCl$_3$): δ 1.01(d, 3H), 1.22(d, 3H), 2.78(s, 3H) 3.86(m, 1H), 4.72(d, 1H), 4.87(d, 1H), 7.24–7.60(m, 7H), 7.68(dt, 1H), 9.25(d, 1H)
Elementary analysis: C$_{22}$H$_{21}$N$_3$O$_2$S; Calcd.: C, 67.50; H, 5.41; N, 10.73 Found: C, 67.17; H, 5.29; N, 10.55

(9) 3-Cyano-N-cyclohexyl-N-isopropyl-2-methylthio-4H-quinolizin-4-one-1-carboxamide, (S-69)
melting point: 204–206° C.
IR (KBr): 2210, 1665, 1625 cm$^{-1}$
NMR (CDCl$_3$): δ 0.85–2.10(m, 16H), 2.78(s, 3H), 3.11(m, 1H), 3.67(m, 1H), 7.25(m, 1H), 7.53(d, 1H), 7.69(m, 1H), 9.23(dd, 1H)
Elementary analysis: C$_{21}$H$_{25}$N$_3$O$_2$S; Calcd.: C, 65.77; H, 6.57; N, 10.96 Found: C, 65.40; H, 6.43; N, 10.75

(10) N-Allyl-3-cyano-N-cyclohexyl-2-methylthio-4H-quinolizin-4-one-1-carboxamide, (S-70)
melting point: 189–191° C.
IR (KBr): 2200, 1670, 1620 cm$^{-1}$
NMR (CDCl$_3$): δ 0.85–2.06(m, 10H), 2.77(s, 3H), 3.25 and 3.73(m, 1H), 4.17 and 4.55(m, 2H), 4.67 and 5.40(d, 1H), 4.77 and 5.25(d, 1H), 5.50 and 6.07(m, 1H), 7.25(m, 1H), 7.50(m, 1H), 7.70(m, 1H), 9.23(t, 1H)

Elementary analysis: $C_{21}H_{23}N_3O_2S$; Calcd.: C, 66.12; H, 6.08; N, 11.01 Found: C, 65.81; H, 6.08; N, 10.80

(11) 3-Cyano-2-methylthio-N-(3-phenylpropyl-4H-quinolizin-4-one-1-carboxamide, (S-71)

melting point: 169.5–171° C.

IR (KBr): 3280, 2210, 1660, 1640, 1625 $cm^{-1}$

NMR (CDCl$_3$): δ 2.06(m, 2H), 2.66(s, 3H), 2.83(t, 2H), 3.59(q, 2H), 6.77(br, 1H), 7.17–7.36(m, 6H), 7.72–7.87(m, 2H), 9.21(d, 1H)

Elementary analysis: $C_{21}H_{19}N_3O_2S$; Calcd.: C, 66.51; H, 4.99; N, 11.13 Found: C, 66.82; H, 5.07; N, 11.31

(12) 3-Cyano-N-cyclohexyl-2-methylthio-4H-quinolizin-4-one-1-carboxamide, (S-72)

melting point: 245–248° C.

IR (KBr): 3280, 2210, 1650, 1620 $cm^{-1}$

NMR (DMSO-d$_6$): δ 1.20–2.10(m, 10H), 2.77(s, 3H), 3.93(m, 1H), 7.67(dt, 1H), 7.81(d, 1H), 8.16(dt, 1H), 8.62(d, 1H), 9.28(d, 1H)

Elementary analysis: $C_{18}H_{19}N_3O_2S$; Calcd.: C, 63.32; H, 5.61; N, 12.31 Found: C, 63.40; H, 5.58; N, 12.16

(13) N-Benzyl-3-cyano-2-methylthio-4H-qunolizin-4-one-1-carboxamide, (S-73)

melting point: 219–221 C.

IR (KBr): 3325, 2210, 1660, 1640, 1620 $cm^{-1}$

NMR (CDCl$_3$): δ 2.59(s, 3H), 4.74(d, 2H), 7.16–7.51(m, 7H), 7.72–7.86(m, 2H), 9.12(d, 1H)

Elementary analysis: $C_{19}H_{15}N_3O_2S$; Calcd.: C, 65.31; H, 4.33; N, 12.03 Found: C, 65.25; H, 4.17; N, 11.49

(14) N-(4-Anilinophenyl)-3-cyano-2-methylthio-4H-quinolizin-4-one-1-carboxamide (S-74)

melting point: >300° C.

IR (KBr): 3350, 3250, 2210, 1660, 1645, 1625 $cm^{-1}$

NMR (DMSO-d$_6$): δ 2.68(s, 3H), 6.79(t, 1H), 7.02–7.27(m, 6H), 7.55–7.64(m, 3H), 7.81(d, 1H), 8.06(dt, 1H), 8.13(brs, 1H), 9.21(d, 1H), 10.05(brs, 1H)

Elementary analysis: $C_{24}H_{18}N_4O_2S$; Calcd.: C, 67.59; H, 4.25; N, 13.14 Found: C, 67.58; H, 4.11; N, 12.97

(15) 3-Cyano-2-methylthio-N-(4-phenyl-2-thiazolyl)-4H-quinolizin-4-one-1-carboxamide, (S-75)

melting point: 183–185° C.

IR (KBr): 3420, 2210, 1660, 1625 $cm^{-1}$

NMR (CDCl$_3$): δ 2.50(s, 3H), 6.79–7.70(m, 9H), 8.92(d, 1H), 13.16(br, 1H)

Elementary analysis: $C_{21}H_{14}N_4O_2S_2$; Calcd.: C, 60.27; H, 3.37; N, 13.39 Found: C, 59.50; H, 3.12; N, 12.96

(16) 3-Cyano-2-methylthio-N-(1,2,3,4-tetrahydro-1-naphthyl)-4H-quinolizin-4-one-1-carboxamide, (S-76)

melting point: 248–250° C.

IR (KBr): 2210, 1665, 1625 $cm^{-1}$

NMR (DMSO-d$_6$): δ 1.72–2.14(m, 4H), 2.67(s, 3H), 2.75(m, 2H), 5.23(q, 1H), 7.07–7.24(m, 3H), 7.48(d, 1H), 7.57(t, 1H), 7.81(d, 1H), 8.09(dt, 1H), 8.95(d, 1H), 9.28(d, 1H)

Elementary analysis: $C_{22}H_{19}N_3O_2S$; Calcd.: C, 67.85; H, 4.92; N, 10.79 Found: C, 67.96; H, 4.91; N, 10.65

(17) 3-Cyano-N-(4-methoxycarbonylbenzyl-2-methylthio-4H-quinolizin-4-one-1-carboxamide, (S-77)

melting point: 206° C.

IR (KBr): 3250, 2200, 1715, 1650, 1620 $cm^{-1}$

NMR (CDCl$_3$): δ 2.58(s, 3H), 3.93(s, 3H), 4.80(d, 2H), 7.33(m, 1H), 7.45(br, 1H), 7.78(d, 2H), 7.71(m, 2H), 8.08(d, 2H), 9.14(d, 1H)

Elementary analysis: $C_{21}H_{17}N_3O_4S$; Calcd.: C, 61.90; H, 4.21; N, 10.31 Found: C, 61.44; H, 4.09; N, 10.25

EXAMPLE 5

3-Cyano-2-methylthio-1-(4-phenylpiperidinocarbonyl)-4H-quinolizin-4-one, (S-78)

A mixture of 590 mg of 4-phenyl-1-(2-pyridylacetyl)-piperidine and 400 mg of methyl 2-cyano-3,3-dimethylthioacrylate was heated at 120° C. for 10 hours. The reaction mixture was chromatographed on a silica gel column using a mixed solvent of dichloromethane, diethyl ether and methanol (1:1:0.1) as an eluent to give 250 mg of 3-cyano-2-methylthio-1-(4-phenylpiperidinocarbonyl)-4H-quinolizin-4-one as pale yellow crystals.

IR (KBr): 2205, 1665, 1620 $cm^{-1}$

Elementary analysis: $C_{23}H_{21}N_3O_2S$; Calcd.: C, 68.46; H, 5.25; N, 10.41 Found: C, 68.43; H, 5.22; N, 10.08

The obtained compound was a mixture of diastereoisomers, then the mixture was separated by means of silica gel column chromatography (eluent: dichloromethane:diethyl ether:methanol=1:1:0.1) to isomer 1 and isomer 2.

isomer 1 (S-78A)

melting point: 187.5–190° C.

NMR (CDCl$_3$): δ 1.40(m, 1H), 1.77(m, 1H), 1.87(m, 1H), 2.14(m, 1H), 2.78(s, 3H), 2.83(dt, 1H), 3.00(dt, 1H), 3.30(dt, 1H), 3.58(dt, 1H), 5.02(dt, 1H), 7.15–7.35(m, 6H), 7.67(d, 1H), 7.78(dt, 1H), 9.26(d, 1H)

isomer 2 (S-78B)

melting point: 196.5–198° C.

NMR (CDCl$_3$): δ 1.80–2.10(m, 4H), 2.78(dt, 1H), 2.83(s, 3H), 2.97(dt, 1H), 3.15(dt, 1H), 3.62(dt, 1H), 5.06(dt, 1H), 7.20–7.35(m, 6H), 7.51(d, 1H), 7.74(dt, 1H), 9.26(d, 1H)

EXAMPLE 6

The following compounds were obtained according to the same procedure as that described in Example 5.

(1) 3-Cyano-2-methylthio-1-piperidinocarbonyl-4H-quinolizin-4-one (S-79)

melting point: 199–200° C.

IR (KBr): 2210, 1660, 1615 $cm^{-1}$

NMR (DMSO-d$_6$): δ 1.35–1.80(m, 6H), 2.77(s, 3H), 3.27–3.56(m, 2H), 3.69(m, 1H), 3.95(m, 1H), 7.67(t, 1H), 7.69(d, 1H), 8.15(dt, 1H), 9.29(d, 1H)

Elementary analysis: $C_{17}H_{17}N_3O_2S$; Calcd.: C, 62.36; H, 5.23; N, 12.83 Found: C, 62.33; H, 5.25; N, 12.58

(2) 1-(4-Acetoxy-4-phenylpiperidinocarbonyl)-3-cyano-methylthio-4H-quinolizin-4-one, (S-80)

melting point: 99–103° C.

IR (KBr): 2210, 1700, 1670, 1625 $cm^{-1}$

NMR (CDCl$_3$): δ 1.77(m, 1H), 1.97(s, 3H), 2.21(m, 1H), 2.48(m, 1H), 2.64(m, 1H), 2.79(s, 3H), 3.28–3.58(m, 3H), 4.39(m, 1H), 7.21–7.44(m, 6H), 7.47(d, 1H), 7.67(dt, 1H), 9.22(d, 1H)

Elementary analysis: $C_{25}H_{23}N_3O_4S$; Calcd.: C, 65.06; H, 5.02; N, 9.10 Found: C, 65.21; H, 5.26; N, 9.31

(3) 3-Cyano-9-methyl-2methylthio-1-(4-phenylpiperidinocarbonyl)-4H-quinolizin-4-one, (S-81)

IR(KBr): 2210, 1675, 1625 $cm^{-1}$

Elementary analysis: $C_{24}H_{23}N_3O_2S$; Calcd.: C, 69.04; H, 5.55; N, 10.06 Found: C, 69.37; H, 5.70; N, 9.74

The obtained compound was a mixture of diastereoisomers, then the mixture was seperated by means of silica gel column chromatography (eluent: dichloromethane:diethyl ether:methanol=1:1:0.1) to isomer 1 and isomer 2.

isomer 1 (S-81A)

melting point: 227–229° C.

NMR (DMSO-d6): δ 1.56–2.12(m, 4H), 2.61(s, 3H), 2.78(s, 3H), 2.87–3.35(m, 3H), 3.89(m, 1H), 4.85(m, 1H), 7.30–7.48(m, 5H), 7.66(t, 1H), 8.08(d, 1H), 9.37(d, 1H)
  isomer 2 (S-81B)
  melting point: 183–186° C.
  NMR (DMSO-d6): δ 1.73–2.08(m, 4H), 2.57(s, 3H), 2.82(s, 3H), 2.87–3.20(m, 3H), 3.73(m, 1H), 4.86(m, 1H), 7.29–7.47(m, 5H), 7.63(t, 1H), 8.08(d, 1H), 9.36(d, 1H)
  (4) 1-(4-Benzylpiperidinocarbonyl)-3-cyano-2-methylthio-4H-quinolizin-4-one (S-82)
  IR (KBr): 2210, 1665, 1625 cm$^{-1}$
  Elementary analysis: $C_{24}H_{23}N_3O_2S$; Calcd.: C, 69.04; H, 5.55; N, 10.06 Found: C, 68.71; H, 5.40; N, 9.65
  The obtained compound was a mixture of diastereoisomers, then the mixture was separated by means of silica gel column chromatography (eluent: dichloromethane:diethyl ether:methanol=1:1:0.1) to isomer 1 and isomer 2.
    isomer 1 (S-82A)
    melting point 106–109° C.
    NMR (CDCl3): δ 0.97(m, 1H), 1.28(m, 1H), 1.65(m, 1H), 1.73–1.94(m, 2H), 2.57(d, 2H), 2.64(s, 3H), 2.83(dt, 1H), 3.10(dt, 1H), 3.43(m, 1H), 4.84(m, 1H), 7.08–7.30(m, 6H), 7.57(d, 1H), 7.72(dt, 1H), 9.23(d, 1H)
    isomer 2 (S-82B)
    melting point: 147–150° C.
    NMR (CDCl3): δ 1.10–1.94(m, 5H), 2.62(d, 2H), 2.79(s, 3H), 2.75–3.00(m, 2H), 3.45(m, 1H), 4.86(m, 1H), 7.08–7.34(m, 6H), 7.43(d, 1H), 7.70(dt, 1H), 9.24(d, 1H)
  (5) 2-Benzylthio-3-cyano-1-(4-phenylpiperidinocarbonyl)-4H-quinolizin-4-one, (S-83)
  IR (KBr): 2210, 1670, 1625 cm$^{-1}$
  Elementary analysis: $C_{29}H_{25}N_3O_2S$; Calcd.: C, 72.63; H, 5.25; N, 8.76 Found: C, 72.58; H, 5.11; N, 8.95
  The obtained compound was a mixture of diastereoisomers, then the mixture was separated by means of silica gel column chromatography (eluent: dichloromethane::diethyl ether:methanol=1:1:0.1) to isomer 1 and isomer 2.
    isomer 1 (S-83A)
    melting point: 190–192° C.
    NMR (CDCl3): δ 1.27(m, 1H), 1.56(m, 1H), 1.80(m, 1H), 1.93(m, 1H), 2.70–2.95(m, 3H), 3.48(m, 1H), 4.40(d, 1H), 4.47(d, 1H), 4.78(m, 1H), 7.18–7.38(m, 10H), 7.60(dt, 1H), 7.79(d, 1H), 8.10(dt, 1H), 9.20(d, 1H)
    isomer 2 (S-83B)
    melting point: 108–110° C.
    NMR (CDCl3): δ 1.60–2.00(m, 4H), 2.81(m, 1H), 2.95–3.15(m, 2H), 3.60(m, 1H), 4.46(d, 1H), 4.54(d, 1H), 4.78(m, 1H), 7.13–7.40(m, 10H), 7.55–7.65(m, 2H), 8.06(dt, 1H), 9.19(d, 1H)
  (6) 1-(4-Benzylpiperidinocarbonyl)-2-benzylthio-3-cyano-4H-quinolizin-4-one, (S-84)
  IR (KBr): 2210, 1670, 1620 cm$^{-1}$
  Elementary analysis: $C_{30}H_{27}N_3O_2S$; Calcd.: C, 73.00; H, 5.51; N, 8.51 Found: C, 72.92; H, 5.32; N, 7.94
  The obtained compound was a mixture of diastereoisomers, then the mixture was separated by means of silica gel column chromatography (eluent: dichloromethane:diethyl ether:methanol=1:1:0.1) to isomer 1 and isomer 2.
    isomer 1 (S-84A)
    melting point: 138–140° C.
    NMR (DMSO-d6): δ 0.85(m, 1H), 1.20–1.75(m, 5H), 2.73(t, 2H), 3.33(m, 2H), 4.37(d, 1H), 4.41(d, 1H), 4.60(m, 1H), 7.12–7.37(m, 10H), 7.53–7.67(m, 2H), 8.06(dt, 1H), 9.19(d, 1H)
    isomer 2 (S-84B)
    melting point 109–111° C.
    NMR (DMSO-d6): δ 1.10–1.80(m, 5H), 2.72(m, 1H), 2.88(m, 2H), 3.20–3.47(m, 2H), 4.46(d, 2H), 4.56(m, 1H), 7.13–7.40(m, 10H), 7.52–7.66(m, 2H), 8.01(dt, 1H), 9.16(d, 1H)
  (7) 3-Cyano-2-methylthio-1-(perhydroindol-1-yl-carbonyl)-4H-quinolizin-4-one, (S-85)
  IR (KBr): 2205, 1665, 1620 cm$^{-1}$
  Elementary analysis: $C_{20}H_{21}N_3O_2S$; Calcd.: C, 65.37; H, 5.76; N, 11.43 Found: C, 65.25; H, 5.71; N, 11.24
  The obtained compound was a mixture of diastereoisomers, then the mixture was separated by means of silica gel column chromatography (eluent: dichloromethane:diethyl ether:methanol=1:1:0.1) to isomer 1 and isomer 2.
    isomer 1 (S-85A)
    melting point: 156–158° C.
    NMR (CDCl3): δ 1.18–2.48(m, 11H), 2.78(s, 3H), 3.10(t, 1H), 3.37(m, 1H), 4.34(m, 1H), 7.26(t, 1H), 754(d, 1H), 7.73(dt, 1H), 9.23(d, 1H)
    isomer 2 (S-85B)
    melting point: 144–146° C.
    NMR (CDCl3): δ 0.90–2.18(m, 10H), 2.47(m, 1H), 2.76(s, 3H), 3.44(m, 1H), 3.78(m, 2H), 7.26(t, 1H), 7.62(d, 1H), 7.70(dt, 1H), 9.22(d, 1H)
  (8) 3-Cyano-2-methylthio-1-(perhydroquinolin-1-ylcarbonyl-4H-quinolizin-4-one, (S-86)
  IR (KBr): 2210, 1670, 1620 cm$^{-1}$
  Elementary analysis: $C_{21}H_{23}N_3O_2S$; Calcd.: C, 66.12; H, 6.08; N, 11.01 Found: C, 66.07; H, 6.13; N, 10.56
  (9) 3-Cyano-2-methylthio-1-(1,2,3,4-tetrahydroisoquinolin-2-ylcarbonyl)-4H-quinolizin-4-one, (S-87)
  melting point: 209° C.
  IR (KBr): 2200, 1670, 1625 cm$^{-1}$
  NMR (CDCl3): δ 2.63 and 2.78(s, 3H), 2.70–3.16(m, 2H), 3.57 and 4.12(m, and t, 2H), 4.37, 4.55, 4.88 and 5.19(d, 2H), 6.88–7.33(m, 5H), 7.54(m, 1H), 7.70(m, 1H), 9.25(d, 1H)
  Elementary analysis: $C_{21}H_{17}N_3O_2S$; Calcd.: C, 67.18; H, 4.56; N, 11.19 Found: C, 67.34; H, 4.50; N, 11.00
  (10) 3-Cyano-2-methylthio-1-(1,2,3,4-tetrahydroquinolin-1-ylcarbonyl)-4H-quinolizin-4-one, (S-88)
  melting point: 214–215.5° C.
  IR (KBr): 2210, 1670, 1630 cm$^{-1}$
  NMR (CDCl3): δ 1.85–2.49(m, 2H), 2.25 and 2.82(s, 3H), 2.87(m, 2H), 3.60 and 4.61(m, 2H), 6.24–8.26(m, 7H), 9.30(d, 1H)
  Elementary analysis: $C_{21}H_{17}N_3O_2S$; Calcd.: C, 67.18; H, 4.56; N, 11.19 Found: C, 66.84; H, 4.45; N, 10.56
  (11) 3-Cyano-2-methylthio-1-(4-piperonyl-1-piperadinyl-carbonyl)-4H-quinolizin-4-one, (S-89)
  melting point: 198–200° C.
  IR (KBr): 2205, 1670, 1625 cm$^{-1}$
  NMR (CDCl3): δ 2.14(m, 1H), 2.52(m, 2H), 2.66(m, 1H), 2.77(s, 3H), 3.25(m, 1H), 3.36(m, 1H), 3.45(s, 2H), 3.83(m, 1H), 3.97(m, 1H), 5.95(s, 2H), 6.74(t, 2H), 6.84(s, 1H), 7.28(dd, 1H), 7.53(d, 1H), 7.74(dt, 1H), 9.23(d, 1H)
  Elementary analysis: $C_{24}H_{22}N_4O_4S$; Calcd.: C, 62.32; H, 4.79; N, 12.11 Found: C, 62.11; H, 4.62; N, 11.82
  (12) 1-(4-Benzyl-1-piperadinylcarbonyl)-3-cyano-2-methylthio-4H-quinolizin-4-one, (S-90)
  melting point: 149–151° C.
  IR (KBr): 2220, 1680, 1625 cm$^{-1}$
  NMR (CDCl3): δ 2.26(m, 1H), 2.54(m, 2H), 2.69(m, 1H), 2.78(s, 3H), 3.26(m, 1H), 3.37(m, 1H), 3.56(s, 2H), 3.85(m, 1H), 3.97(m, 1H), 7.24–7.37(m, 6H), 7.54(d, 1H), 7.73(dt, 1H), 9.24(d, 1H)

Elementary analysis: $C_{23}H_{22}N_4O_2S$; Calcd.: C, 66.01; H, 5.30; N, 13.39 Found: C, 65.98; H, 5.03; N, 13.25

(13) 3-Cyano-2-methylthio-1-(4-phenyl-1-piperadinylcarbonyl)-4H-quinolizin-4-one, (S-91)

melting point: 255–256° C.

IR (KBr): 2220, 1670, 1625 cm$^{-1}$

NMR (CDCl$_3$): δ 2.79(s, 3H), 3.00(m, 1H), 3.21–3.57(m, 5H), 4.02(m, 1H), 4.12(m, 1H), 6.90–6.99(m, 3H), 7.26–7.34(m, 3H), 7.56(d, 1H), 7.75(dt, 1H), 9.25(d, 1H)

Elementary analysis: $C_{22}H_{20}N_4O_2S$; Calcd.: C, 65.33; H, 4.98; N, 13.85 Found: C, 65.25; H, 5.91; N, 13.69

EXAMPLE 7

1-Acetyl-3-cyano-2-methylthio-4H-quinolizin-4-one, (S-92)

A mixture of 153 mg of methyl 2-pyridylmethyl ketone and 230 mg of methyl 2-cyano-3,3-dimethylthioacrylate was heated at 120° C. for 10 hours. The reaction mixture was chromatographed on a silica gel column using a mixed solvent of dichloromethane and diethyl ether (1:1) as an eluent to give 85 mg of 1-acetyl-3-cyano-2-methylthio-4H-quinolizin-4-one as pale yellow crystals.

melting point: 177.5–178° C.

IR (KBr): 2210, 1690, 1650, 1615 cm$^{-1}$

NMR (CDCl$_3$): δ 2.69(s, 3H), 2.74(s, 3H), 7.34(dt, 1H), 7.64(d, 1H), 7.78(dt, 1H), 9.31(d, 1H)

Elementary analysis: $C_{13}H_{10}N_2O_2S$; Calcd.: C, 60.45; H, 3.90; N, 10.85 Found: C, 60.41; H, 3.91; N, 10.69

EXAMPLE 8

The following compounds were obtained according to the same procedure as that described in Example 7.

(1) 1-Butyryl-3-cyano-2-methylthio-4H-quinolizin-4-one, (S-93)

melting point: 142–144° C.

IR (KBr): 2205, 1695, 1660, 1620 cm$^{-1}$

NMR (CDCl$_3$): δ 1.04(t, 3H), 1.80(m, 2H), 2.73(s, 3H), 2.91(t, 2H), 7.33(dd, 1H), 7.53(d, 1H), 7.76(dt, 1H), 9.30(d,

Elementary analysis: $C_{15}H_{14}N_2O_2S$; Calcd.: C, 62.92; H, 4.93; N, 9.78 Found: C, 62.55; H, 4.88; N, 6.92

(2) 3-Cyano-1-cyclohexylacetyl-2-methylthio-4H-quinolizin-4-one, (S-94)

melting point: 159–160° C.

IR (KBr): 2205, 1695, 1660, 1620 cm$^{-1}$

NMR (CDCl$_3$): δ 0.96–2.11(m, 11H), 2.72(s, 3H), 2.83(d, 2H), 7.32(dt, 1H), 7.53(d, 1H), 7.76(dt, 1H), 9.30(d, 1H)

Elementary analysis: $C_{19}H_{20}N_2O_2S$; Calcd.: C, 67.03; H, 5.92; N, 8.23 Found: C, 68.18; H, 5.97; N, 8.00

(3) 3-Cyano-2-methylthio-1-phenylacetyl-4H-quinolizin-4-one, (S-95)

melting point: 165–168° C.

IR (KBr): 2210, 1705, 1675, 1620 cm$^{-1}$

NMR (CDCl$_3$): δ 2.75(s, 3H), 4.26(s, 2H), 7.14–7.33(m, 7H), 7.56(dt, 1H), 9.24(d, 1H)

Elementary analysis: $C_{19}H_{14}N_2O_2S$; Calcd.: C, 68.24; H, 4.22; N, 8.38 Found: C, 67.68; H, 4.08; N, 8.20

(4) 1-(4-Chlrophenylacetyl)-3-cyano-2-methylthio-4H-quinolizin-4-one, 9S-96)

melting point: 168–171° C.

IR (KBr): 2210, 1700, 1660, 1620 cm$^{-1}$

NMR (CDCl$_3$): δ 2.76(s, 3H), 4.23(s, 2H) 7.18(d, 2H), 7.27–7.33(m, 4H), 7.65(dt, 1H), 9.27(d, 1H)

Elementary analysis: $C_{19}H_{13}N_2O_2SCl$; Calcd.: C, 61.87; H, 3.55; N, 7.59 Found: C, 61.97; H, 3.56; N, 7.13

(5) 3-Cyano-1-(3-methylphenylacetyl)-2-methylthio-4H-quinolizin-4-one, (S-97)

melting point: 150–152° C.

IR (KBr): 2210, 1700, 1660, 1620 cm$^{-1}$

NMR (CDCl$_3$): δ 2.29(s, 3H), 2.77(s, 3H), 4.22(s, 2H), 6.95–7.29(m, 6H), 7.57(dt, 1H), 9.24(d, 1H)

Elementary analysis: $C_{20}H_{16}N_2O_2S$; Calcd.: C, 68.94; H, 4.63; N, 8.04 Found: C, 68.76; H, 4.46; N, 7.61

(6) 3-Cyano-1-(2-methylphenylacetyl)-2-methylthio-4H-quinolizin-4-one, (S-98)

melting point: 154–156° C.

IR (KBr): 2205, 1700, 1660, 1615 cm$^{-1}$

NMR (CDCl$_3$): δ 2.32(s, 3H), 2.75(s, 3H), 4.30(s, 2H), 7.05–7.16(m, 5H), 7.25(dt, 1H), 7.56(dt, 1H), 9.24(d, 1H)

Elementary analysis: $C_{20}H_{16}N_2O_2S$; Calcd.: C, 68.94; H, 4.63; N, 8.04 Found: C, 69.22; H, 4.56; N, 7.77

(7) 3-Cyano-1-(4-methylphenylacetyl)-2-methylthio-4H-quinolizin-4-one, (S-99)

melting point: 169–171° C.

IR (KBr): 2205, 1690, 1665, 1620 cm$^{-1}$

NMR (CDCl$_3$): δ 2.30(s, 3H), 2.74(s, 3H), 4.23(s, 2H), 7.09(brs, 4H), 7.18–7.28(m, 2H), 7.56(dt, 1H), 9.24(d, 1H)

Elementary analysis: $C_{20}H_{16}N_2O_2S$; Calcd.: C, 68.94; H, 4.63; N, 8.04 Found: C,68.43; H,4.48; N, 7.97

(8) 3-Cyano-1-(2,4dimethylphenylacetyl)-2-methylthio-4H-quinolizin-4-one, (S-100)

melting point: 148–151° C.

IR (KBr): 2205, 1700, 1660, 1625 cm$^{-1}$

NMR (CDCl$_3$): δ 2.27(s, 6H), 2.75(s, 3H), 4.26(s, 2H), 6.87–7.28(m, 5H), 7.57(dt, 1H), 9.25(d, 1H)

Elementary analysis: $C_{21}H_{18}N_2O_2S$; Calcd.: C, 69.59; H, 5.01; N, 7.73 Found: C, 68.81; H, 4.98; N, 7.54

(9) 3-Cyano-1-(3,4-dimethylphenylacetyl)-2-methylthio-4H-quinolizin-4-one, (S-101)

melting point: 161–164° C.

IR (KBr): 2205, 1695, 1665, 1620 cm$^{-1}$

NMR (CDCl$_3$): δ 2.19(s, 3H), 2.20(s, 3H), 2.74(s, 3H), 4.17(s, 2H), 6.87–7.28(m, 5H), 7.58(dt, 1H), 9.24(d, 1H)

Elementary analysis: $C_{21}H_{18}N_2O_2S$; Calcd.: C, 69.59; H, 5.01; N, 7.73 Found: C, 69.25; H, 5.07; N, 7.64

(10) 3-Cyano-1-(4-methoxyphenylacetyl)-2-methylthio-4H-quinolizin-4-one, (S-102)

melting point: 165–168° C.

IR (KBr): 2210, 1705, 1660, 1625 cm$^{-1}$

NMR (CDCl$_3$): δ 2.74(s, 3H), 3.77(s, 3H), 4.19(s, 2H), 6.79(d, 2H), 7.11(d, 2H, 7.20(d, 1H), 7.27(m, 1H), 7.58(dt, 1H), 9.24(d, 1H)

Elementary analysis: $C_{20}H_{16}N_2O_3S$; Calcd.: C, 65.92; H, 4.43; N, 7.69 Found: C, 66.05; H, 4.32; N, 7.25

(11) 3-Cyano-2-mehtylthio-1-(1-naphthylacetyl)-4H-quinolizin-4-one, (S-103)

melting point: 210–212° C.

IR (KBr): 2200, 1705, 1650, 1620 cm$^{-1}$

NMR (CDCl$_3$): δ 2.28(s, 3H), 4.76(s, 2H), 6.83(d, 1H), 7.11(dt, 1H), 7.12–7.54(m, 6H), 7.72(d, 1H), 7.80(d, 1H), 9.13(d, 1H)

Elementary analysis: $C_{23}H_{16}N_2O_2S$; Calcd.: C, 71.86; H, 4.19; N, 7.29 Found: C, 71.48; H, 4.04; N, 7.07

(12) 3-Cyano-2-methylthio-1-(3-phenylpropionyl)-4H-quinolizin-4-one, (S-104)

melting point: 112–114° C.

IR (KBr): 2205, 1695, 1670, 1620 cm$^{-1}$

NMR (CDCl$_3$): δ 2.68(s, 3H), 3.13(t, 2H), 7.16–7.33(m, 7H), 7.59(dt, 1H), 9.26(d, 1H)

Elementary analysis: $C_{20}H_{16}N_2O_2S$; Calcd.: C, 68.94; H, 4.63; N, 8.04 Found: C, 69.10; H, 4.60; N, 7.66

(13) 3-Cyano-2-methylthio-1-(4-phenylbutyryl)-4H-quinolizin-4one, (S-105)

melting point: 64–66° C.

IR (KBr): 2210, 1700, 1665, 1625 cm$^{-1}$

NMR (CDCl$_3$): δ 2.13(m, 2H), 2.62(s, 3H), 2.76(t, 2H), 2.89(t, 2H), 7.16–7.35(m, 6H), 7.47(d, 1H), 7.72(dt, 1H), 9.28(d, 1H)

Elementary analysis: C$_{21}$H$_{18}$N$_2$O$_2$S; Calcd.: C, 69.59; H, 5.01; N, 7.73 Found: C, 69.59; H, 4.93; N, 7.63

(14) 3-Cyano-2-methylthio-1-(4-thienylbutyryl)-4H-quinolizin-4-one, (S-106)

melting point: 93–95° C.

IR (KBr): 2210, 1690, 1670, 1630 cm$^{-1}$

NMR (CDCl$_3$): δ 2.17(m, 2H), 2.66(s, 3H), 2.95(t, 2H), 2.98(t, 2H), 6.81(d, 1H), 6.93(t, 1H), 7.14(d, 1H), 7.32(dt, 1H), 7.48(d, 1H), 7.73(dt, 1H), 9.28(d, 1H)

Elementary analysis: C$_{19}$H$_{16}$N$_2$O$_2$S$_2$; Calcd.: C, 61.93; H, 4.38; N, 7.60 Found: C, 61.94; H, 4.29; N, 7.46

(15) 3-Cyano-2-methylthio-1-(5-phenylvaleryl)-4H-quinolizin-4-one, (S-107)

melting point: 89–91° C.

IR (KBr): 2200, 1695, 1660, 1620 cm$^{-1}$

NMR (CDCl$_3$): δ 1.68–1.88(m, 4H), 2.67(t, 2H), 2.70(s, 3H), 2.94(t, 2H), 7.14–7.33(m, 6H), 7.48(d, 1H), 7.73(dt, 1H), 9.29(d, 1H)

Elementary analysis: C$_{22}$H$_{20}$N$_2$O$_2$S; Calcd.: C, 70.19; H, 5.35; N, 7.44 Found: C, 70.53; H, 5.38; N, 7.43

(16) 3-Cyano-8-methyl-2-methylthio-1-(5-phenylvaleryl)-4H-quinolizin-4-one, (S-108)

melting point: 111–113° C.

IR (KBr): 2200, 1695, 1660, 1635 cm$^{-1}$

NMR (CDCl$_3$): δ 1.68–1.89(m, 4H), 2.49(s, 3H), 2.67(t, 2H), 2.68(s, 3H), 2.93(t, 2H), 7.12–7.32(m, 7H), 9.19(d, 1H)

Elementary analysis: C$_{23}$H$_{22}$N$_2$O$_2$S; Calcd.: C, 70.74; H, 5.68; N, 7.17 Found: C, 70.91; H, 5.64; N, 7.27

(17) 3-Cyano-2-methylthio-1-(1-phenyl-4-piperidylacetyl)-4-quinolizin-4-one, (S-109)

melting point: 150–151° C.

IR (KBr): 2210, 1690, 1675, 1630 cm$^{-1}$

NMR (CDCl$_3$): δ 1.38(M, 2H), 1.82(brd, 2H), 2.06(m, 3H), 2.73(s, 3H), 2.86(d, 2H), 2.89(brd, 2H), 7.20–7.36(m, 6H), 7.50(d, 1H), 7.76(dt, 1H), 9.29(d, 1H)

Elementary analysis: C$_{24}$H$_{23}$N$_3$O$_2$S; Calcd.: C, 69.04; H, 5.55; N, 10.06 Found: C, 69.29; H, 5.73; N, 10.01

TEST EXAMPLE

Determination of Igs produced in in vitro culture

BALB/c mice were immunized intraperitoneally with 5 μg of DNP-As adsorbed in 4 mg aluminum hydroxide gel. 4 weeks after the immunization, the spleens were excised from the mice and $5 \times 10^7$ spleen cells were transferred intravenously into the recipient mice which had been exposed to 600 rad of X-ray irradiation. Immediately after cell transfer, the recipients were then immunized intraperitoneally with 5 μg of DNP-As adsorbed in 4 mg aluminum hydroxide gel to induce adoptive secondary immune response. Further 4 weeks after the immunization of recipients, the spleens were excised from them and the spleen cell suspensions $5 \times 10^6$ cells/ml were cultured with or without a compound to be tested in 96-well micro plates at 37° C. for 4 days. IgE and IgG secreted into the culture supernatant was each determined correspondingly by ELISA and the inhibitory effect was calculated according to the following equation.

$$\text{inhibition \%} = \frac{\text{average amount of } Ig \text{ in control group} - \text{average amount of } Ig \text{ in test group}}{\text{average amount of } Ig \text{ in control group}} \times 100$$

The results obtained were shown below:

| Comp. No. | Concentration (μg/ml) | Inhibition % of IgE | Inhibition % of IgG |
|---|---|---|---|
| S-1 | 5.0 | 65 | 22 |
| S-2 | 5.0 | 51 | 27 |
| S-3 | 1.0 | 79 | 35 |
| S-4 | 1.0 | 68 | 39 |
| S-5 | 20.0 | 77 | 47 |
| S-6 | 10.0 | 63 | 35 |
| S-7 | 40.0 | 52 | 24 |
| S-8 | 2.5 | 36 | 18 |
| S-9 | 2.5 | 54 | 17 |
| S-10 | .2.5 | 48 | 27 |
| S-11 | 5.0 | 66 | 30 |
| S-12 | 5.0 | 65 | 32 |
| S-13 | 5.0 | 67 | 9 |
| S-14 | 1.0 | 69 | 39 |
| S-15 | 40.0 | 62 | 21 |
| S-16 | 5.0 | 52 | 14 |
| S-17 | 0.25 | 43 | 7 |
| S-18 | 2.5 | 54 | 34 |
| S-19 | 5.0 | 71 | 27 |
| S-20 | 5.0 | 84 | 52 |
| S-21 | 5.0 | 70 | 47 |
| S-22 | 40.0 | 82 | 42 |
| S-23 | 1.0 | 79 | 34 |
| S-24 | 40.0 | 77 | 54 |
| S-25 | 5.0 | 75 | 54 |
| S-26 | 40.0 | 48 | 17 |
| S-27 | 2.5 | 56 | 16 |
| S-28 | 2.5 | 49 | 24 |
| S-29 | 1.0 | 69 | 31 |
| S-30 | 0.25 | 45 | 27 |
| S-31 | 40.0 | 34 | 3 |
| S-32 | 1.0 | 52 | 28 |
| S-33 | 20.0 | 81 | 47 |
| S-34 | 0.25 | 52 | 31 |
| S-35 | 1.0 | 64 | 45 |
| S-36 | 0.25 | 33 | 8 |
| S-37 | 0.25 | 36 | 11 |
| S-38 | 1.0 | 77 | 43 |
| S-39 | 1.0 | 65 | 31 |
| S-40 | 0.25 | 53 | 34 |
| S-41 | 1.0 | 86 | 68 |
| S-42 | 1.0 | 75 | 43 |
| S-43 | 1.0 | 75 | 46 |
| S-44 | 1.0 | 54 | 18 |
| S-45 | 5.0 | 71 | 16 |
| S-46 | 1.0 | 90 | 79 |
| S-47 | 40.0 | 60 | 28 |
| S-48 | 1.0 | 57 | 15 |
| S-49 | 1.0 | 80 | 56 |
| S-50 | 1.0 | 64 | 42 |
| S-51 | 1.0 | 65 | 43 |
| S-52 | 0.25 | 46 | 17 |
| S-53 | 0.25 | 69 | 49 |
| S-54 | 1.0 | 73 | 50 |
| S-55 | 0.25 | 51 | 29 |
| S-56 | 5.0 | 70 | 30 |
| S-57 | 5.0 | 53 | 32 |
| S-58 | 10.0 | 89 | 60 |
| S-59 | 40.0 | 74 | 49 |
| S-60 | 1.0 | 58 | 25 |
| S-61 | 2.5 | 93 | 48 |
| S-62 | 40.0 | 64 | 36 |
| S-63 | 40.0 | 85 | 47 |
| S-64 | 5.0 | 65 | 41 |
| S-65 | 2.5 | 87 | 40 |
| S-66 | 40.0 | 64 | 35 |
| S-67 | 2.5 | 68 | 46 |
| S-68 | 2.5 | 41 | 7 |
| S-69 | 2.5 | 56 | 22 |
| S-70 | 5.0 | 65 | 32 |
| S-71 | 5.0 | 63 | 35 |
| S-72 | 5.0 | 46 | −5 |

-continued

| Comp. No. | Concentration (μg/ml) | Inhibition % of IgE | Inhibition % of IgG |
|---|---|---|---|
| S-73 | 40.0 | 55 | 24 |
| S-74 | 2.5 | 51 | 10 |
| S-75 | 2.5 | 50 | 25 |
| S-76 | 2.5 | 37 | 1 |
| S-77 | 5.0 | 34 | 10 |
| S-78 | 2.5 | 60 | 16 |
| S-79 | 40.0 | 59 | 13 |
| S-80 | 2.5 | 66 | 34 |
| S-81A | 1.0 | 46 | 17 |
| S-81B | 1.0 | 50 | 4 |
| S-82B | 2.5 | 63 | 8 |
| S-82A | 1.0 | 43 | 18 |
| S-83A | 1.0 | 67 | 23 |
| S-83B | 0.25 | 41 | 10 |
| S-84A | 1.0 | 58 | 22 |
| S-84B | 1.0 | 58 | 32 |
| S-85A | 5.0 | 43 | 23 |
| S-85B | 2.5 | 39 | 19 |
| S-86 | 2.5 | 46 | 21 |
| S-87 | 5.0 | 61 | 36 |
| S-88 | 2.5 | 40 | 7 |
| S-89 | 5.0 | 58 | 32 |
| S-90 | 5.0 | 45 | 14 |
| S-91 | 2.5 | 39 | 11 |
| S-92 | 40.0 | 56 | 8 |
| S-93 | 10.0 | 62 | 31 |
| S-94 | 1.0 | 62 | 33 |
| S-95 | 20.0 | 70 | 47 |
| S-96 | 5.0 | 41 | 12 |
| S-97 | 2.5 | 46 | 18 |
| S-98 | 10.0 | 38 | 13 |
| S-99 | 10.0 | 52 | 1 |
| S-100 | 2.5 | 63 | 34 |
| S-101 | 40.0 | 58 | 13 |
| S-102 | 10.0 | 52 | 20 |
| S-103 | 2.5 | 49 | 15 |
| S-104 | 2.5 | 66 | 39 |
| S-105 | 1.0 | 65 | 21 |
| S-106 | 1.0 | 61 | 26 |
| S-107 | 1.0 | 80 | 43 |
| S-108 | 1.0 | 60 | 35 |
| S-109 | 1.0 | 77 | 54 |

What is claimed is:

1. A 4H-quinolizin-4-one compound corresponding to the formula:

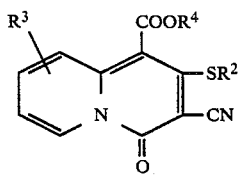

where $R^2$ is an alkyl, alkenyl or aralkyl group having up to 18 carbon atoms; $R^3$ is hydrogen or an alkyl group having 1 to 6 carbon atoms; $R^4$ is a substituent having up to 16 carbon atoms which is alkenyl, alkynyl, cycloalkyl, cycloalkyl-alkyl, cycloalkenyl, cycloalkyl-alkenyl, aralkyl, aralkenyl, aryloxyalkyl or arylthioalkyl.

2. A 4H-quinolizin-4-one compound corresponding to the formula:

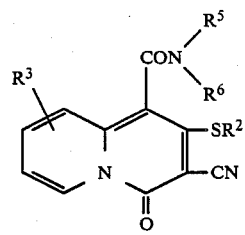

where $R^2$ is an alkyl, alkenyl or aralkyl group having up to 18 carbon atoms; $R^3$ is hydrogen or an alkyl group having 1 to 6 carbon atoms; $R^5$ and $R^6$ individually is hydrogen or a substituent having up to 8 carbon atoms which is alkyl, alkenyl, cycloalkyl, aryl, aralkyl, arylaminoalkyl or arylthiozolyl, and $R^5$ and $R^6$ taken together with the connecting nitrogen atom form a piperidino, perhydro-indol-1-yl, perhydro-quinolizin-1-yl, 4-arylpiperazin-1-yl, 4-aralkylpiperazin-1-yl, 1,2,3,4-tetrahydroisoquinolin-2-yl or 1,2,3,4-tetrahydroquinolin-1-yl group having 4 to 12 carbon atoms.

3. A 4H-quinolizin-4-one compound corresponding to the formula:

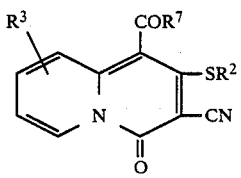

where $R^2$ is an alkyl, alkenyl or aralkyl group having up to 18 carbon atoms; $R^3$ is hydrogen or an alkyl group having 1 to 6 carbon atoms; and $R^7$ is a substituent having up to 12 carbon atoms which is alkyl, cycloalkyl-alkyl, aralkyl, arylpiperidinyl or thienylalkyl.

4. A method for the treatment of allergic bronchial asthma, allergic rhinitis, atopic dermatitis and hypersensitiveness diseases associated with immunoglobulin E-antibody formation in a mammal which comprises administering an effective dosage from about 0.1 mg to 10 mg per Kg of mammal weight by oral administration or from about 0.02 mg to 5 mg per Kg of mammal weight by parenteral administration per day of an immunoglobulin E-antibody formation-inhibiting 4H-quinolizin-4-one compound to the mammal.

5. A method in accordance with claim 4 wherein the 4H-quinolizin-4-one compound corresponds to the formula represented in claim 1.

6. A method in accordance with claim 5 wherein the 4H-quinolizin-4one compound corresponds to the formula represented in claim 2.

7. A method in accordance with claim 5 wherein the 4H-quinolizin-4-one compound corresponds to the formula represented in claim 3.

8. A pharmaceutical composition for the treatment of allergic bronchial asthma, allergic rhinitis, atopic dermatitis and hypersensitiveness diseases associated with immunoglobulin E-antibody formation in a mammal, which composition contains an effective dosage from about 0.1 mg to 10 mg per Kg of mammal weight for oral administration or from about 0.02 mg to 5 mg per Kg of mammal weight for parenteral administration per day of an immunoglobulin E formation-inhibiting 4H-quinolizin-4-one compound.

9. A pharmaceutical composition in accordance with claim 8 wherein the 4H-quinolizin-4-one compound corresponds to the formula represented in claim 1, or a pharmaceutically acceptable salt thereof.

10. A pharmaceutical composition in accordance with claim 8 wherein the 4H-quinolizin-4-one compound corresponds to the formula represented in claim 2, or a pharmaceutically acceptable salt thereof.

11. A pharmaceutical composition in accordance with claim 8 wherein the 4H-quinolizin-4-one compound corresponds to the formula represented in claim 3, or a pharmaceutically acceptable salt thereof.

12. 4H-Quinolizin-4-one derivatives selected from the group consisting of cyclohexylmethyl 3-cyano-2-methylthio-4H-quinolizin-4-one-1-carboxylate; cyclopropylmethyl 3-cyano-2methylthio-4H-quinolizin-4-one-1-carboxylate; 3'-cyclohexylpropyl 3-cyano-2methylthio-4H-quinolizin-4-one-1-carboxylate; 2', 2', 2'-trichloroethyl 3-cyano-2-methylthio-4H-quinolizin-4-one-1-carboxylate; 2'-propenyl 3-cyano-2-methylthio-4H-quinolizin-4-one-1-carboxylate; 2'-propynyl 3-cyano-2-methylthio-4H-quinolizin-4-one-1-carboxylate; cyclopentyl 3-cyano-2-methylthio-4H-quinolizin-4-one-1-carboxylate; cyclobutyl 3-cyano-2-methylthio-4H-quinolizin-4-one-1-carboxylate; cyclohexyl 3-cyano-2-methylthio-4H-quinolizin-4-one-1-carboxylate; 2'-cyclohexenyl 3-cyano-2-methylthio-4H-quinolizin-4-one-1-carboxylate; trans-4'-hydroxycyclohexyl 3-cyano-2-methylthio-4H-quinolizin-4-one-1carboxylate; 2'-methylcyclohexyl 3-cyano-2-methylthio-4H-quinolizin-4-one-1-carboxylate; cyclohexyl 3cyano-8-methyl-2-methylthio-4H-quinolizin-4-one-1-carboxylate; cycloheptyl 3-cyano-2-methylthio-4H-quinolizin-4-one-1-carboxylate; cyclooctyl 3-cyano-2-methylthio-4H-quinolizin-4-one-1-carboxylate; 2'-adamantyl 3-cyano-2-methylthio-4H-quinolizin-4-one-1-carboxylate; 1',2',3',4'-tetrahydro-1'-naphthyl 3-cyano-2-methylthio-4H-quinolizin-4one-1-carboxylate; 4°-bromobenzyl 3-cyano-2-methylthio-4H-quinolizin-4-one-1-carboxylate; 1'-phenylethyl 3-cyano-2-methylthio-4H-quinolizin-4-one-1-carboxylate; 3',4'-dimethylbenzyl 3-cyano-2-methylthio-4H-quinolizin-4-one-1-carboxylate; piperonyl 3-cyano-2-methylthio-4H-quinolizin-4-one-1-carboxylate; 3',4',5'-trimethoxybenzyl 3 cyano-2-methylthio-4H-quinolizin-4-one-1-carboxylate; benzyl 3-cyano-8-methyl-2-methylthio-4H-quinolizin-4-one-1-carboxylate; benzyl 3-cyano-2methylthio-4H-quinolizin-4-one-1-carboxylate; 1'-(4-bromophenyl)ethyl 3-cyano-2-methylthio-4H-quinolizin-4-one-1-carboxylate; 4'methoxybenzyl 3-cyano-2-methylthio-4H-quinolizin-4-one-1-carboxylate; 1'-(4-cyanophenyl)ethyl 3cyano-2-methylthio-4H-quinolizin-4-one-1-carboxylate; 4'-ethoxybenzyl 3-cyano-2-methylthio-4H-quinolizin-4-one-1-carboxylate; 4'-fluorobenzyl 3-cyano-2-methylthio-4H-quinolizin-4-one-1-carboxylate; 3'-methoxybenzyl 3-cyano-2-methylthio-4H-quinolizin-4-one-1-carboxylate; 4'-isopropylbenzyl 3-cyano-2-methylthio-4H-quinolizin-4-one-1-carboxylate; 2'-methoxybenzyl 3-cyano-2-methylthio-4H-quinolizin-4-one-1-carboxylate; 3'-chlorobenzyl 3-cyano-2-methylthio-4H-quinolizin-4-one-1-carboxylate; 2'-chlorobenzyl 3cyano-2-methylthio-4H-quinolizin-4-one-1-carboxylate; 4'-phenylbenzyl 3-cyano-2-methylthio-4H-quinolizin-4-one-1-carboxylate; 2'-naphthylmethyl 3-cyano-2-methylthio-4H-quinolizin-4-one-1-carboxylate; 1'-naphthylmethyl 3-cyano-2-methylthio-4H-quinolizin-4-one-1-carboxylate; 1'-methyl-2'-phenylethyl 3-cyano-2-methylthio-4H-quinolizin-4-one-1-carboxylate; 2',2'-diphenylethyl 3-cyano-2-methylthio-4H-quinolizin-4-one-1-carboxylate; 3'-phenylpropyl 3-cyano-2-methylthio-4H-quinolizin-4-one-1-carboxylate; 1'-methyl-3'-phenylpropyl 3-cyano-2-methylthio-4H-quinolizin-4-one-1-carboxylate; trans-cinnamyl 3-cyano-2-methylthio-4H-quinolizin-4-one-1-carboxylate; 2'-phenylethyl 3-cyano-2-methylthio-4H-quinolizin-4-one-1-carboxylate; 4'-phenylbutyl 3-cyano-2-methylthio-4H-quinolizin-4-one-1-carboxylate; 2'-phenylethyl 3 cyano-8-methyl-2-methylthio-4H-quinolizin-4-one-1-carboxylate; 3'-phenylpropyl 3-cyano-8-methyl-2-methylthio-4H-quinolizin-4-one-1-carboxylate; 3'phenylpropyl 3-cyano-2-ethylthio-4H-quinolizin-4-one-1-carboxylate; 2'-(4-chlorophenoxy)ethyl 3-cyano-2-methylthio-4H-quinolizin-4-one-1-carboxylate; 3'-phenoxypropyl 3-cyano-2-methylthio-4H-quinolizin-4-one-1-carboxylate; 2'-phenylthioethyl 3-cyano-2-methylthio-4H-quinolizin-4-one-1-carboxylate; ethyl 3-cyano-2-methallylthio-4H-quinolizin-4-one-1-carboxylate; ethyl 3-cyano-2isopropylthio-4H-quinolizin-4-one-1-carboxylate; ethyl 3-cyano-2-butylthio-4H-quinolizin-4-one-1-carbxylate; ether 3-cyano-2-benzylthio-4H-quinolizin-4-one-1-carboxylate; 3-cyano-N,N-dibenzyl-2-methylthio-4H-quinolizin-4-one-1-carboxamide; 3-cyano-N,N-dicyclohexyl-2-methylthio-4H-quinolizin-4-one-1-carboxamide; 3-cyano-N,N-diethyl-2-methylthio-4H-quinolizin-4-one-1-carboxamide; 3-cyano-N,N-diisopropyl-2-methylthio-4H-quinolizin-4-one-1-carboxamide; 3-cyano-N,N-diisobutyl-2-methylthio-4H-quinolizin-4-one-1-carboxamide; 3-cyano-N,N-dihexyl-2-methylthio-4H-quinolizin-4-one-1-carboxamide; N-benzyl-3-cyano-N-methyl-2-methylthio-4H-quinolizin-4-one-1-carboxamide; 3-cyano-2-methylthio-N-phenyl-N-(2-phenylaminoethyl)-4H-quinolizin-4-one-1-carboxamide; N-benzyl-3-cyano-N-isopropyl-2-methylthio-4H-quinolizin-4-one-1-carboxamide; 3-cyano-N-cyclohexyl-N-isopropyl-2-methylthio-4H-quinolizin-4-one-1-carboxamide; N-allyl-3-cyano-N-cyclohexyl-2-methylthio-4H-quinolizin-4-one- 1-carboxamide; 3-cyano-2-methylthio-N-(3-phenylpropyl)-4H-quinolizin-4-one-1-carboxamide; 3-cyano-N-cyclohexyl-2-methylthio-4H-quinolizin-4-one-1-carboxamide; N-benzyl-3-cyano-2-methylthio-4H-quinolizin-4-one-1-carboxamide; N-(4-anilinophenyl)-3-cyano-2-methylthio-4H-quinolizin-4-one-1-carboxamide; 3-cyano-2-methylthio-N-(4-phenyl-2-thiazolyl)-4-quinolizin-4-one-1-carboxamide; 3-cyano-2-methylthio-N-(1,2,3,4-tetrahydro-1-naphthyl)-4H-quinolizin-4-one-1-carboxamide; 3-cyano-N-(4-methoxycarbonylbenzyl)-2-methylthio-4H-quinolizin-4-one-1-carboxamide; 3-cyano-2-methylthio-1-(4-phenylpiperidinocarbonyl)-4H-quinolizin-4-one; 3-cyano-2-methylthio-1-piperidinocarbonyl-4H-quinolizin-4-one; 1-(4-acetoxy-4-phenylpiperidinocarbonyl)-3-cyano-2-methylthio4H-quinolizin-4-one; 3-cyano-9-methyl-2-methylthio-1-(4-phenylpiperidinocarbonyl)-4H-quinolizin-4-one; 1-(4-benzylpiperidinocarbonyl)-3-cyano-2-methylthio-4H-quinolizin-4-one; 2-benzylthio-3-cyano-1-(4-phenylpiperdinocarbonyl)-4H-quinolizin-4-one; 1-(4-benzylpiperidinocarbonyl)-2-benzylthio-3-cyano-4H-quinolizin -4-one; 3-cyano-2-methylthio-1-(perhydroindol-1-ylcarbonyl)-4H-quinolizin-4-one; 3-cyano-2-methylthio-1-(perhydroquinolin-1-ylcarbonyl)-4H-quinolizin-4-one; 3-cyano-2-methylthio-1-(1,2,3,4,-tetrahydroisoquinolin-2-ylcarbonyl)-4H-quinolizin-4-one; 3-cyano-2-methylthio-1-( 1,2,3,4-tetrahydroquinolin-1-ylcarbonyl)-4H-quinolizin-4-one; 3-cyano-2-methylthio-1-(4-piperonyl-1-piperidinyl-carbonyl)-4H-quinolizin-4-one; 1-(4-benzyl-1-piperidinylcarbonyl)-3-cyano-2-methylthio-4H-quinolizin-4-one;

3-cyano-2-methylthio-1-(4-phenyl-1-piperidinylcarbonyl)-4H-quinolizin-4-one; 1-acetyl-3-cyano-2-methylthio-4H-quinolizin-4-one; 1-butyryl-3-cyano-2-methylthio-4H-quinolizin-4-one; 3-cyano-1-cyclohexylacetyl-2-methylthio-4H-quinolizin-4-one; 3-cyano-2-methylthio-1-phenylacetyl-4H-quinolizin-4-one; 1-(4-chlorophenylacetyl)-3-cyano-2-methylthio-4H-quinolizin-4-one; 3-cyano-1-(3-methylphenylacetyl)-2-methylthio-4H-quinolizin-4-one; 3-cyano-1-(2-methylphenylacetyl)-2-methylthio-4H-quinolizin-4-one; 3-cyano-1-(4-methylphenylacetyl)-2-methylthio-4H-quinolizin-4-one; 3-cyano-1-(2,4-dimethylphenylacetyl)-2-methylthio-4H-quinolizin-4-one; 3-cyano-1-(3,4-dimethylphenylacetyl)-2-methylthio-4H-quinolizin-4-one; 3-cyano-1-(4-methoxyphenylacetyl)-2-methylthio-4H-quinolizin-4-one; 3-cyano-2-methylthio-1-(1-naphthylacetyl)-4H-quinolizin-4-one; 3-cyano-2-methylthio-1-(3-phenylpropionyl)-4H-quinolizin-4-one; 3-cyano-2-methylthio-1-(4-phenylbutyryl)-4H-quinolizin-4-one; 3-cyano-2-methylthio-1-(4-thienylbutyryl)-4H-quinolizin-4-one; 3-cyano-2-methylthio-1-(5-phenylvaleryl)-4H-quinolizin-4-one; 3-cyano-8-methyl-2-methylthio-1-(5-phenylvaleryl)-4H-quinolizin-4-one; 3-cyano-2-methylthio-1-(1-phenyl-4-piperidylacetyl)-4H-quinolizin-4-one; or a pharmaceutically acceptable salt thereof.

* * * * *